US011987833B2

(12) United States Patent
Seo et al.

(10) Patent No.: US 11,987,833 B2
(45) Date of Patent: May 21, 2024

(54) METHOD FOR PRODUCING MULTI-HYDROXY DERIVATIVES OF POLYUNSATURATED FATTY ACIDS

(71) Applicant: KOREA RESEARCH INSTITUTE OF BIOSCIENCE AND BIOTECHNOLOGY, Daejeon (KR)

(72) Inventors: Jeong Woo Seo, Daejeon (KR); Jong Jae Yi, Daejeon (KR); Sun Yeon Heo, Daejeon (KR); Young Bae Kim, Daejeon (KR); Chul Ho Kim, Daejeon (KR); Baek Rock Oh, Daejeon (KR); Jung Hyun Ju, Daejeon (KR); Hack Sun Choi, Jeju-si (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 823 days.

(21) Appl. No.: 17/072,696

(22) Filed: Oct. 16, 2020

(65) Prior Publication Data

US 2021/0040518 A1 Feb. 11, 2021

Related U.S. Application Data

(63) Continuation-in-part of application No. PCT/KR2019/004583, filed on Apr. 16, 2019.

(30) Foreign Application Priority Data

Apr. 16, 2018 (KR) ........................ 10-2018-0043972
May 4, 2018 (KR) ........................ 10-2018-0051695
Nov. 19, 2018 (KR) ........................ 10-2018-0142895
Nov. 19, 2018 (KR) ........................ 10-2018-0142896

(51) Int. Cl.

*C12P 7/64* (2022.01)
*A61P 35/00* (2006.01)
*C11C 3/00* (2006.01)
*C12N 9/02* (2006.01)
*C12P 7/6427* (2022.01)
*C12P 17/02* (2006.01)

(52) U.S. Cl.

CPC ............. *C12P 7/6427* (2013.01); *A61P 35/00* (2018.01); *C11C 3/00* (2013.01); *C12N 9/0069* (2013.01); *C12P 17/02* (2013.01)

(58) Field of Classification Search

CPC .................................... C12P 7/64; C12N 9/02
See application file for complete search history.

(56) References Cited

U.S. PATENT DOCUMENTS 7,884,131 B2 2/2011 Arterburn et al.
9,404,095 B2 8/2016 Liu et al.
9,624,477 B2 4/2017 Cirpus et al.
10,233,167 B2 3/2019 Serhan et al.
10,233,168 B2 3/2019 Serhan et al.
10,239,850 B2 3/2019 Serhan et al.
10,568,858 B2 2/2020 Bannenberg et al.
10,711,288 B2 7/2020 Schirmer et al.
11,077,083 B2 8/2021 Bannenberg et al.
11,077,084 B2 8/2021 Bannenberg et al.
2005/0075398 A1 4/2005 Bazan et al.
2006/0241088 A1 10/2006 Arterburn et al.
2011/0178047 A1 7/2011 Arterburn et al.
2011/0190389 A1 8/2011 Arterburn et al.
2011/0288317 A1 11/2011 Serhan et al.
2012/0059061 A1 3/2012 Arita et al.
2012/0136057 A1 5/2012 Ritchie et al.
2015/0119460 A1 4/2015 Serhan et al.
2015/0126602 A1 5/2015 Bannenberg et al.
2016/0130616 A1 5/2016 Schirmer et al.
2017/0022526 A1 1/2017 Ogawa et al.
2018/0271818 A1 9/2018 Bannenberg et al.
2019/0201363 A1 7/2019 Bannenberg et al.
2019/0256876 A1 8/2019 Ogawa et al.
2020/0281883 A1 9/2020 Bannenberg et al.
2021/0154163 A1 5/2021 Bannenberg et al.
2021/0285020 A1 9/2021 Ogawa et al.
2022/0042051 A1 2/2022 Han et al.

FOREIGN PATENT DOCUMENTS

CN 101102988 A 1/2008
CN 101663031 A 3/2010
CN 107075502 A 8/2017
CN 113286890 A 8/2021
CN 114729335 A 7/2022
JP 6046345 B2 12/2016
KR 10-2007-0090928 A 9/2007
KR 10-2012-0046754 A 5/2012
KR 10-2016-0017427 A 2/2016
KR 10-2016-0020516 A 2/2016

(Continued)

OTHER PUBLICATIONS

Charles N. Serhan et al., "Anti-Inflammatory Actions of Neuroprotectin D1/Protectin D1 and Its Natural Stereoisomers: Assignments of Dihydroxy-Containing Docosatrienes1", The Journal of Immunology, 2006, pp. 1848-1859.

M. Aursnes et al., "Stereoselective synthesis of protectin D1: A potent antiinflammatory and proresolving lipid mediator", Org Biomol Chem., Jan. 21, 2014, 12(3): 432-437, 14 Pages.

Eleanor P. Dobson et al., "Controlled formation of mono- and dihydroxy-resolvins from EPA and DHA using soybean 15-lipoxygenase", Journal of Lipid Research, Mar. 2013, vol. 54, pp. 1439-1447.

(Continued)

*Primary Examiner* — Tekchand Saidha
(74) *Attorney, Agent, or Firm* — Hauptman Ham, LLP

(57) ABSTRACT

The present invention relates to a novel enzyme capable of producing multi-hydroxy derivatives from polyunsaturated fatty acids and a method for producing multi-hydroxy derivatives of polyunsaturated fatty acids using the same.

4 Claims, 17 Drawing Sheets

Specification includes a Sequence Listing.

(56) References Cited

FOREIGN PATENT DOCUMENTS

| | | | |
|---|---|---|---|
| WO | 2012026106 | A1 | 1/2012 |
| WO | 2013-170006 | A2 | 11/2013 |

OTHER PUBLICATIONS

Min-Ji Kim et al., "Production of 8, 11-Dihydroxy and 8-Hydroxy Unsaturated Fatty Acids from Unsaturated Fatty Acids by Recombinant *Escherichia coli* Expressing 8,11-Linoleate Diol Synthase from Penicillium Chrysogenum", Biotechnol. Prog., vol. 33, No. 2, Jan. 5, 2017, pp. 390-396.

Igor A. Butovich et al., "Novel Oxylipins Formed from Docosahexaenoic Acid by Potato Lipoxygenase—10(S)-Hydroxydocosahexaenoic Acid and 10,20-Dihydroxydocosahexaenoic Acid", Lipids, vol. 40, No. 3, 2005, pp. 249-257.

"Arachidonate 15-lipoxygenase [Oscillatoria nigro-viridis]", NCBI Reference Sequence: WP_015178512.1; 2 pages.

Zhujun Zhu et al., "A Lipoxygenase from Red Alga *Pyropia haitanensis*, a Unique Enzyme Catalyzing the Free Radical Reactions of Polyunsaturated Fatty Acids with Triple Ethylenic Bonds", PLOS One | DOI:10.1371/journal.pone.0117351; Feb. 6, 2015; 20 Pages.

Charles N. Serhan et al., "Resolvins and Protectins in Inflammation-Resolution", Chem Rev., Oct. 12, 2011, 111(10); 44 Pages.

Jun Miyata et al., "Role of omega-3 fatty acids and their metabolites in asthma and allergic diseases", Allergology International 64, 2015, pp. 27-34.

Narihito Ogawa et al., "Total Synthesis of Resolvin D5", The Journal of Organic Chemistry, Japan, Jan. 18, 2017, 31 Pages.

Joseph T. O'Flaherty et al., "15-Lipoxygenase Metabolites of Docosahexaenoic Acid Inhibit Prostate Cancer Cell Proliferation and Survival", PLOS One, vol. 7, Issue 9, Sep. 2012, 8 Pages.

International Search Report dated May 28, 2020, corresponding to International Application No. PCT/KR2019/004583.

Megan L. Sulciner et al., "Resolvins suppress tumor growth and enhance cancer therapy", The Journal of Experimental Medicine. vol. 215, No. 1, Nov. 30, 2017, pp. 115-140, cited in NPL No. 5.

Charles N. Serhan et al., "Resolvins: A Family of Bioactive Products of Omega-3 Fatty Acid Transformation Circuits Initiated by Aspirin Treatment that Counter Proinflammation Signals", Journal of Experimental Medicine, Rockafeller University Press, US, vol. 196, No. 8, Oct. 21, 2002, pp. 1025-1037, cited in NPL No. 5.

Jong-Jae Yi et al., "Synthesis of two new lipid mediators from docosahexaenoic acid by combinatorial catalysis involving enzymatic and chemical reaction", Scientific Reports, vol. 10, No. 1, Nov. 2, 2020, cited in NPL No. 5.

Database Uniprot, Online, Mar. 6, 2013, cited in NPL No. 5.

Extended European Search Report dated Dec. 22, 2021, corresponding to European Application No. 19788644.3.

Office Action dated Aug. 12, 2023, in connection with Chinese Patent Application No. 201980025785.9; with English translation (17 pages).

Gugger et al., "Arachidonate 15-lipoxygenase [Oscillatoria nigro-viridis PCC 7112]," Sequence ID: AFZ09286.1, Dec. 6, 2012 (3 pages); Cited in NPL No. 1.

Zhang et al, "Progress in Anti-inflammation Effect of n-3 Fatty Acid Metabolites," Progress in Biochemistry and Biophysics, 2011, vol. 38, No. 1, pp. 20-27; with English abstract; Cited in NPL No. 1.

Zhu et al, "Research progress on regressin and inflammation," Journal of Hebei Medical university, Feb. 2018, vol. 39, No. 2 (13 pages); with English translation; Cited in NPL No. 1.

Gong et al., "The Metabolism of Polyunsaturated Fatty Acids and Its Regulation to Inflammation," Chinese Journal of Animal Nutrition, 2017, vol. 29, No. 1, pp. 1-7; with English abstract; Cited in NPL No. 1.

SEQUENCE LISTING

```
<160> NUMBER OF SEQ ID NOS: 6

<210> SEQ ID NO 1
<211> LENGTH: 571
<212> TYPE: PRT
<213> ORGANISM: Artificial Sequence
<220> FEATURE:
<223> OTHER INFORMATION: K9V_A296G

<400> SEQUENCE: 1

Met Val Asp Asn Met Lys Pro Ser Leu Pro Gln Asp Asp Pro Asn Gln
1               5                   10                  15

Glu Gln Arg Lys Asp Ser Leu Asn Arg Gln Gln Gln Ala Tyr Gln Phe
            20                  25                  30

Asp Tyr Glu Ser Leu Ser Pro Leu Ala Leu Leu Lys Asn Val Pro Ala
        35                  40                  45

Val Glu Asn Phe Ser Ser Lys Tyr Ile Gly Glu Arg Ile Leu Ala Thr
    50                  55                  60

Ser Glu Leu Pro Ala Asn Met Leu Ala Ala Asp Ser Arg Thr Phe Leu
65                  70                  75                  80

Asp Pro Leu Asp Glu Leu Gln Asp Tyr Glu Asp Phe Phe Thr Leu Leu
```

-continued

```
                85                  90                  95

Pro Leu Pro Ala Val Ala Lys Ile Tyr Gln Thr Asp Arg Ser Phe Ala
            100                 105                 110

Glu Gln Arg Leu Ser Gly Ala Asn Pro Met Val Leu Arg Leu Leu Asp
        115                 120                 125

Ala Gly Asp Pro Arg Ala Gln Thr Leu Ala Gln Ile Ser Ser Phe His
    130                 135                 140

Pro Leu Phe Asp Leu Gly Gln Glu Leu Gln Gln Lys Asn Ile Tyr Val
145                 150                 155                 160

Ala Asp Tyr Thr Gly Thr Asp Glu His Tyr Arg Ala Pro Ser Lys Ile
                165                 170                 175

Gly Gly Gly Ser Tyr Glu Lys Gly Arg Lys Phe Leu Pro Lys Pro Arg
            180                 185                 190

Ala Phe Phe Ala Trp Arg Trp Thr Gly Ile Arg Asp Arg Gly Glu Met
        195                 200                 205

Thr Pro Ile Ala Ile Gln Leu Asp Pro Thr Pro Asp Ser His Val Tyr
    210                 215                 220

Thr Pro Phe Asp Pro Pro Val Asp Trp Leu Phe Ala Lys Leu Cys Val
225                 230                 235                 240

Gln Val Ala Asp Ala Asn His His Glu Met Ser Ser His Leu Gly Arg
                245                 250                 255

Thr His Leu Val Met Glu Pro Ile Ala Ile Val Thr Ala Arg Gln Leu
            260                 265                 270

Ala Gln Asn His Pro Leu Ser Leu Leu Leu Lys Pro His Phe Arg Phe
        275                 280                 285

Met Leu Thr Asn Asn Glu Leu Gly Arg Ser Tyr Leu Ile Ala Pro Gly
    290                 295                 300

Gly Pro Val Asp Glu Leu Leu Gly Gly Thr Leu Pro Glu Thr Met Glu
305                 310                 315                 320

Ile Ala Arg Glu Ala Cys Ser Thr Trp Ser Leu Asp Glu Phe Ala Leu
                325                 330                 335

Pro Ala Glu Leu Lys Asn Arg Gly Met Asp Asp Thr Asn Gln Leu Pro
            340                 345                 350

His Tyr Pro Tyr Arg Asp Asp Gly Leu Leu Leu Trp Asp Ala Ile Glu
        355                 360                 365

Thr Phe Val Ser Gly Tyr Leu Lys Phe Phe Tyr Pro Thr Glu Ile Ala
    370                 375                 380

Ile Val Gln Asp Val Glu Leu Gln Thr Trp Ala Gln Glu Leu Ala Ser
385                 390                 395                 400

Asp Arg Gly Gly Lys Val Lys Gly Met Pro Pro Arg Ile Asn Thr Val
                405                 410                 415

Glu Gln Leu Ile Lys Ile Val Thr Thr Ile Ile Phe Thr Cys Gly Pro
            420                 425                 430

Gln His Ser Ala Val Asn Phe Pro Gln Tyr Glu Tyr Met Ser Phe Ala
        435                 440                 445

Ala Asn Met Pro Leu Ala Ala Tyr Arg Asp Ile Pro Lys Ile Thr Ala
    450                 455                 460

Ser Gly Asn Leu Glu Val Ile Thr Glu Lys Asp Ile Leu Arg Leu Leu
465                 470                 475                 480

Pro Pro Tyr Lys Arg Ala Ala Asp Gln Leu Lys Ile Leu Phe Thr Leu
                485                 490                 495

Ser Ala Tyr Arg Tyr Asp Arg Leu Gly Tyr Tyr Asp Lys Ser Phe Arg
            500                 505                 510
```

```
Glu Leu Tyr Arg Met Ser Phe Asp Glu Val Phe Ala Gly Thr Pro Ile
        515                 520                 525

Gln Leu Leu Ala Arg Gln Phe Gln Gln Asn Leu Asn Met Ala Glu Gln
    530                 535                 540

Lys Ile Asp Ala Asn Asn Gln Lys Arg Val Ile Pro Tyr Ile Ala Leu
545                 550                 555                 560

Lys Pro Ser Leu Val Ile Asn Ser Ile Ser Met
                565                 570


<210> SEQ ID NO 2
<211> LENGTH: 571
<212> TYPE: PRT
<213> ORGANISM: Artificial Sequence
<220> FEATURE:
<223> OTHER INFORMATION: enzyme (K9V)

<400> SEQUENCE: 2

Met Val Asp Asn Met Lys Pro Ser Leu Pro Gln Asp Asp Pro Asn Gln
1               5                   10                  15

Glu Gln Arg Lys Asp Ser Leu Asn Arg Gln Gln Gln Ala Tyr Gln Phe
            20                  25                  30

Asp Tyr Glu Ser Leu Ser Pro Leu Ala Leu Leu Lys Asn Val Pro Ala
        35                  40                  45

Val Glu Asn Phe Ser Ser Lys Tyr Ile Gly Glu Arg Ile Leu Ala Thr
    50                  55                  60

Ser Glu Leu Pro Ala Asn Met Leu Ala Ala Asp Ser Arg Thr Phe Leu
65                  70                  75                  80

Asp Pro Leu Asp Glu Leu Gln Asp Tyr Glu Asp Phe Phe Thr Leu Leu
                85                  90                  95

Pro Leu Pro Ala Val Ala Lys Ile Tyr Gln Thr Asp Arg Ser Phe Ala
            100                 105                 110

Glu Gln Arg Leu Ser Gly Ala Asn Pro Met Val Leu Arg Leu Leu Asp
        115                 120                 125

Ala Gly Asp Pro Arg Ala Gln Thr Leu Ala Gln Ile Ser Ser Phe His
    130                 135                 140

Pro Leu Phe Asp Leu Gly Gln Glu Leu Gln Gln Lys Asn Ile Tyr Val
145                 150                 155                 160

Ala Asp Tyr Thr Gly Thr Asp Glu His Tyr Arg Ala Pro Ser Lys Ile
                165                 170                 175

Gly Gly Gly Ser Tyr Glu Lys Gly Arg Lys Phe Leu Pro Lys Pro Arg
            180                 185                 190

Ala Phe Phe Ala Trp Arg Trp Thr Gly Ile Arg Asp Arg Gly Glu Met
        195                 200                 205

Thr Pro Ile Ala Ile Gln Leu Asp Pro Thr Pro Asp Ser His Val Tyr
    210                 215                 220

Thr Pro Phe Asp Pro Pro Val Asp Trp Leu Phe Ala Lys Leu Cys Val
225                 230                 235                 240

Gln Val Ala Asp Ala Asn His His Glu Met Ser Ser His Leu Gly Arg
                245                 250                 255

Thr His Leu Val Met Glu Pro Ile Ala Ile Val Thr Ala Arg Gln Leu
            260                 265                 270

Ala Gln Asn His Pro Leu Ser Leu Leu Leu Lys Pro His Phe Arg Phe
        275                 280                 285

Met Leu Thr Asn Asn Glu Leu Ala Arg Ser Tyr Leu Ile Ala Pro Gly
    290                 295                 300
```

```
Gly Pro Val Asp Glu Leu Leu Gly Gly Thr Leu Pro Glu Thr Met Glu
305                 310                 315                 320

Ile Ala Arg Glu Ala Cys Ser Thr Trp Ser Leu Asp Glu Phe Ala Leu
                325                 330                 335

Pro Ala Glu Leu Lys Asn Arg Gly Met Asp Asp Thr Asn Gln Leu Pro
            340                 345                 350

His Tyr Pro Tyr Arg Asp Asp Gly Leu Leu Leu Trp Asp Ala Ile Glu
        355                 360                 365

Thr Phe Val Ser Gly Tyr Leu Lys Phe Phe Tyr Pro Thr Glu Ile Ala
    370                 375                 380

Ile Val Gln Asp Val Glu Leu Gln Thr Trp Ala Gln Glu Leu Ala Ser
385                 390                 395                 400

Asp Arg Gly Gly Lys Val Lys Gly Met Pro Pro Arg Ile Asn Thr Val
                405                 410                 415

Glu Gln Leu Ile Lys Ile Val Thr Thr Ile Ile Phe Thr Cys Gly Pro
            420                 425                 430

Gln His Ser Ala Val Asn Phe Pro Gln Tyr Glu Tyr Met Ser Phe Ala
        435                 440                 445

Ala Asn Met Pro Leu Ala Ala Tyr Arg Asp Ile Pro Lys Ile Thr Ala
    450                 455                 460

Ser Gly Asn Leu Glu Val Ile Thr Glu Lys Asp Ile Leu Arg Leu Leu
465                 470                 475                 480

Pro Pro Tyr Lys Arg Ala Ala Asp Gln Leu Lys Ile Leu Phe Thr Leu
                485                 490                 495

Ser Ala Tyr Arg Tyr Asp Arg Leu Gly Tyr Tyr Asp Lys Ser Phe Arg
            500                 505                 510

Glu Leu Tyr Arg Met Ser Phe Asp Glu Val Phe Ala Gly Thr Pro Ile
        515                 520                 525

Gln Leu Leu Ala Arg Gln Phe Gln Gln Asn Leu Asn Met Ala Glu Gln
    530                 535                 540

Lys Ile Asp Ala Asn Asn Gln Lys Arg Val Ile Pro Tyr Ile Ala Leu
545                 550                 555                 560

Lys Pro Ser Leu Val Ile Asn Ser Ile Ser Met
                565                 570
```

<210> SEQ ID NO 3
<211> LENGTH: 1716
<212> TYPE: DNA
<213> ORGANISM: Artificial Sequence
<220> FEATURE:
<223> OTHER INFORMATION: K9V_A296G

<400> SEQUENCE: 3

```
atggtagaca atatgaaacc gtctcttcct caagacgacc cgaaccaaga acagcgcaag     60

gactccttga atcgccagca gcaagcttat cagtttgact atgagagttt atcaccattg    120

gcattattga aaaacgtgcc cgcagttgag aacttttcgt caaagtatat tggggaaaga    180

atattagcaa catcggaact tccagcaaat atgctggcag cggattctag aacttttctg    240

gatcctctcg atgaactcca agattatgag gatttcttta ctctgctgcc gctgcctgct    300

gttgctaaaa tttaccaaac cgatcgctct ttcgcagaac agcgcctgtc tggagcaaac    360

ccgatggtgc ttcgtctgtt agatgccggc gatccgcggg cgcaaacact ggcacaaatt    420

tccagctttc atccattatt cgatctgggc caagagttgc agcaaaaaaa catttatgtg    480

gccgattaca cgggtactga cgaacactat cgcgcgccgt caaagatagg aggcgggagc    540
```

```
tatgaaaaag gcagaaaatt cctgccgaaa ccgcgggctt ttttcgcatg gcggtggacg    600
gggattcgcg atcgcggtga aatgacacca attgccatac aactagatcc cacgccagat    660
agccatgtct acaccccatt cgaccctcct gtggattggc tgtttgcgaa actctgtgtg    720
caagtagcag atgccaatca ccatgaaatg agctcgcatt taggtcgtac gcatctggtg    780
atggaaccaa ttgcgatcgt aaccgcccgt cagttggccc aaaatcatcc gctgagcctg    840
ttgctgaaac cgcactttcg ctttatgctt accaacaacg agctgggacg ttcttatcta    900
atcgctcccg gtgggcccgt cgacgaactt ctaggcggta ctcttccaga aacaatggag    960
atagctagag aggcttgtag tacctggagt ctcgatgagt ttgcgttgcc cgccgaactg   1020
aaaaatcgtg gcatggatga cacaaatcag ctgcctcact atccgtatcg agacgatgga   1080
cttctgcttt gggatgcgat agagacgttt gtttccggct atctgaaatt cttttatccg   1140
acggagatcg cgatcgtaca agatgttgaa ctgcagacct gggcccaaga attagcgtcc   1200
gataggggcg gtaaggtcaa aggaatgcct ccacgcatca ataccgttga acagttaatt   1260
aaaatcgtga caactataat tttcacctgc ggtccgcagc attcagcagt caactttcca   1320
cagtatgaat acatgagttt tgccgccaat atgccgttgg cagcgtaccg tgatattccc   1380
aaaattactg cttcaggcaa tctcgaagtt ataacagaaa aagacatctt acggctttta   1440
cctccgtaca aacgagcggc tgaccagctg aaaattctgt ttactctgtc agcttatagg   1500
tatgaccgtt tgggttacta cgataaatct tttcgtgaac tgtatcggat gagtttcgat   1560
gaggtttttg caggaacccc gatccagctt ttagcccgtc agttccagca gaacttaaat   1620
atggcagaac aaaagattga tgccaacaat caaaagcgag ttattcctta cattgctctc   1680
aagccttcct tggtaatcaa tagcatcagt atgtaa                             1716
```

```
<210> SEQ ID NO 4
<211> LENGTH: 1716
<212> TYPE: DNA
<213> ORGANISM: Artificial Sequence
<220> FEATURE:
<223> OTHER INFORMATION: enzyme (K9V)

<400> SEQUENCE: 4
```

```
atggtagaca atatgaaacc gtctcttcct caagacgacc cgaaccaaga acagcgcaag     60
gactccttga atcgccagca gcaagcttat cagtttgact atgagagttt atcaccattg    120
gcattattga aaaacgtgcc cgcagttgag aacttttcgt caaagtatat tggggaaaga    180
atattagcaa catcggaact tccagcaaat atgctggcag cggattctag aacttttctg    240
gatcctctcg atgaactcca agattatgag gatttcttta ctctgctgcc gctgcctgct    300
gttgctaaaa tttaccaaac cgatcgctct ttcgcagaac agcgcctgtc tggagcaaac    360
ccgatggtgc ttcgtctgtt agatgccggc gatccgcggg cgcaaacact ggcacaaatt    420
tccagctttc atccattatt cgatctgggc caagagttgc agcaaaaaaa catttatgtg    480
gccgattaca cgggtactga cgaacactat cgcgcgccgt caaagatagg aggcgggagc    540
tatgaaaaag gcagaaaatt cctgccgaaa ccgcgggctt ttttcgcatg gcggtggacg    600
gggattcgcg atcgcggtga aatgacacca attgccatac aactagatcc cacgccagat    660
agccatgtct acaccccatt cgaccctcct gtggattggc tgtttgcgaa actctgtgtg    720
caagtagcag atgccaatca ccatgaaatg agctcgcatt taggtcgtac gcatctggtg    780
atggaaccaa ttgcgatcgt aaccgcccgt cagttggccc aaaatcatcc gctgagcctg    840
```

-continued

```
ttgctgaaac cgcactttcg ctttatgctt accaacaacg agctggcacg ttcttatcta    900

atcgctcccg gtgggcccgt cgacgaactt ctaggcggta ctcttccaga aacaatggag    960

atagctagag aggcttgtag tacctggagt ctcgatgagt ttgcgttgcc cgccgaactg   1020

aaaaatcgtg gcatggatga cacaaatcag ctgcctcact atccgtatcg agacgatgga   1080

cttctgcttt gggatgcgat agagacgttt gtttccggct atctgaaatt cttttatccg   1140

acggagatcg cgatcgtaca agatgttgaa ctgcagacct gggcccaaga attagcgtcc   1200

gataggggcg gtaaggtcaa aggaatgcct ccacgcatca ataccgttga acagttaatt   1260

aaaatcgtga caactataat tttcacctgc ggtccgcagc attcagcagt caactttcca   1320

cagtatgaat acatgagttt tgccgccaat atgccgttgg cagcgtaccg tgatattccc   1380

aaaattactg cttcaggcaa tctcgaagtt ataacagaaa aagacatctt acggctttta   1440

cctccgtaca aacgagcggc tgaccagctg aaaattctgt ttactctgtc agcttatagg   1500

tatgaccgtt tgggttacta cgataaatct tttcgtgaac tgtatcggat gagtttcgat   1560

gaggtttttg caggaacccc gatccagctt ttagcccgtc agttccagca gaacttaaat   1620

atggcagaac aaaagattga tgccaacaat caaaagcgag ttattcctta cattgctctc   1680

aagccttcct tggtaatcaa tagcatcagt atgtaa                             1716


<210> SEQ ID NO 5
<211> LENGTH: 34
<212> TYPE: DNA
<213> ORGANISM: Artificial Sequence
<220> FEATURE:
<223> OTHER INFORMATION: forward primer for both Seq ID No. 3 and Seq
      ID No. 4

<400> SEQUENCE: 5

catatggtag acaatatgaa accgtctctt cctc                                 34


<210> SEQ ID NO 6
<211> LENGTH: 34
<212> TYPE: DNA
<213> ORGANISM: Artificial Sequence
<220> FEATURE:
<223> OTHER INFORMATION: reverse primer for both Seq ID No. 3 and Seq
      ID No. 4

<400> SEQUENCE: 6

cttggtaatc aatagcatca gtatgtaact cgag                                 34
```

METHOD FOR PRODUCING MULTI-HYDROXY DERIVATIVES OF POLYUNSATURATED FATTY ACIDS

CROSS-REFERENCE TO RELATED APPLICATION

The present application is a continuation-In-Part of International Application No. PCT/KR2019/004583, filed Apr. 16, 2019, which is based upon and claims priority to (1) Patent Application No. 10-2018-0043972 filed in Korea on Apr. 16, 2018, (2) Patent Application No. 10-2018-0051695 filed in Korea on May 4, 2018, (3) Patent Application No. 10-2018-0142895 filed in Korea on Nov. 19, 2018, and (4) Patent Application No. 10-2018-0142896 filed in Korea on Nov. 19, 2018, all of which are incorporated herein by reference in their entireties.

TECHNICAL FIELD

The present invention relates to an enzyme capable of producing multi-hydroxy derivatives from polyunsaturated fatty acids and a method for producing multi-hydroxy derivatives of polyunsaturated fatty acids using the same.

BACKGROUND ART

Since an inflammatory response plays an important role as a body's primary defense against pathogen infection and various toxic substances, but at the same time, can act as an underlying factor causing various chronic diseases, the inflammatory response is a physiological phenomenon that needs to be strictly controlled by a sophisticated regulatory mechanism in vivo.

Prostaglandin or leukotriene, a derivative of arachidonic acid (C20: 4n-6), which corresponds to an omega-6 polyunsaturated fatty acid, is a representative inflammatory response initiation signal substance and induces an imbalance in the inflammatory response capable of causing various chronic diseases in vivo. In general, the inflammatory response is recognized to be naturally terminated when the inflammatory response initiation signal material is not produced, and various steroidal or non-steroidal anti-inflammatory therapeutic agents have been developed to inhibit the production of the substance. However, in recent years, the termination mechanism of the inflammatory response is also performed through a sophisticated regulatory process, and in the process, it was confirmed that hydroxy derivatives of omega-3 polyunsaturated fatty acids, such as docosahexaenoic acid (DHA, C22: 6n-3) and eicosapentaenoic acid (EPA, C20: 5n-3) may serve as a signaling substance acting in the termination mechanism of the inflammatory response. Those hydroxy derivatives that act as the signal substance for the termination mechanism of the inflammatory response were referred to as specialized proresolving mediators (SPMs; resolvins, protectins, maresins). It was confirmed that these hydroxy derivatives exhibit an effect superior to existing anti-inflammatory therapeutic agents such as corticosteroids and non-steroid anti-inflammatory drug (NSAID), aspirin.

In addition, unlike conventional steroidal or non-steroidal anti-inflammatory therapeutic agents, which mainly induce inhibition of the production of the inflammatory response initiation signal substance, the SPM has an advantage of showing the efficacy over all stages of the inflammatory response. Thus, researches are actively underway on the presence or absence of therapeutic efficacy using the SPM, with respect to various diseases, such as various chronic inflammatory diseases (various chronic inflammatory diseases such as vascular, myocardial infarction, stroke, dementia, osteoarthritis, lung diseases including asthma, gastroenteritis, periodontitis, dry eye syndrome, and fatty liver), infection sepsis, burns, wound recovery, pain, cancer, and diabetes.

On the other hand, the SPM, an inflammatory response termination signal substance in vivo, has a structure in which two or three hydroxyl groups are inserted into omega-3 polyunsaturated fatty acids, and it is known that the SPM is produced in a very trace amount through a continuous action of two or more enzymes. Therefore, in order to produce SPM sufficient for developing the efficacy and the therapeutic agent of the inflammatory response termination signal substance, efforts to be produced through an organic synthesis process are continued (see Non-Patent Document 1), but there is a limitation that the process thereof is very complicated.

Recently, it has been reported that mono-hydroxy or di-hydroxy derivative of omega-3 polyunsaturated fatty acids may be produced by using a soybean 15-lipoxygenase enzyme, potato lipoxygenase, or algae lipoxygenase (see Non-Patent Documents 2 to 4).

However, in addition to the above enzymes, research on novel enzymes capable of producing the SPM has been continuously conducted.

PRIOR ART DOCUMENTS (Non-Patent Document 1) Ogawa et al., *J. Org. Chem.*, 82(4), 2032-2039 (2017)

(Non-Patent Document 2) Dobson et al., Journal of Lipid Research, 54, 1439-1447 (2013)

(Non-Patent Document 3) Butovich et al., Lipids, 40(3), 249-257 (2005)

(Non-Patent Document 4) Zhu et al., PLOS ONE, 10(2), e0117351 (2015)

DISCLOSURE

Technical Problem

An object of the present invention is to provide an enzyme capable of producing multi-hydroxy derivatives from polyunsaturated fatty acids and a method capable of producing multi-hydroxy derivatives of polyunsaturated fatty acids in vivo or in vitro using the same.

Technical Solution

In order to achieve the object, an aspect of the present invention provides an enzyme for producing a di-hydroxy derivative of polyunsaturated fatty acids having an amino acid sequence of SEQ ID NO: 1.

Another aspect of the present invention provides an enzyme for producing a tri-hydroxy or tetra-hydroxy derivative of polyunsaturated fatty acids having an amino acid sequence of SEQ ID NO: 2.

Yet another aspect of the present invention provides a method for producing multi-hydroxy derivatives of polyunsaturated fatty acids in vitro, comprising reacting the enzyme for producing the di-hydroxy derivative or the enzyme for producing the tri-hydroxy or tetra-hydroxy derivative with polyunsaturated fatty acids, for example, docosahexaenoic acid.

Still another aspect of the present invention provides a method for producing multi-hydroxy derivatives in vivo, comprising incubating a transformant, in which a gene encoding the enzyme for producing the di-hydroxy derivative or the enzyme for producing the tri-hydroxy or tetra-hydroxy derivative is transduced, in the presence of polyunsaturated fatty acids, for example, docosahexaenoic acid, and isolating multi-hydroxy derivatives from the incubated culture medium.

Advantageous Effects

According to the present invention, the enzyme can produce multi-hydroxy derivatives such as di-hydroxy, tri-hydroxy, or tetra-hydroxy in a single reaction by using polyunsaturated fatty acids as a substrate and can be very effectively used for ex vivo production of multi-hydroxy derivatives.

However, the effects of the present invention are not limited to the above-mentioned effects, and other effects not mentioned will be clearly understood by those skilled in the art from the following description.

DESCRIPTION OF DRAWINGS

In FIGS. 2A and 2B, 9R-HODE refers to 9R-hydroxy-octadecadienoic acid, and 13S-HODE refers to 13S-hydroxy-octadecadienoic acid, respectively.

FIG. 5B illustrates a chemical structural formula of a mono-hydroxy derivative produced by the protein having the amino acid sequence of SEQ ID NO: 1. In addition, FIGS. 5C to 5E illustrate chemical structures of derivatives confirmed by the results of NMR analysis on reaction products obtained by reacting a protein having an amino acid sequence of SEQ ID NO: 2 with docosahexaenoic acid. Wherein, FIG. 5C illustrates a chemical structural formula of a tetra-hydroxy derivative produced by the protein having the amino acid sequence of SEQ ID NO: 2, FIG. 5D illustrates a chemical structural formula of a mono-hydroxy derivative produced by the protein having the amino acid sequence of SEQ ID NO: 2, and FIG. 5E illustrates a chemical structural formula of a di-hydroxy derivative produced by the protein having the amino acid sequence of SEQ ID NO: 2, respectively. In addition.

BEST MODE

Figure 1A:
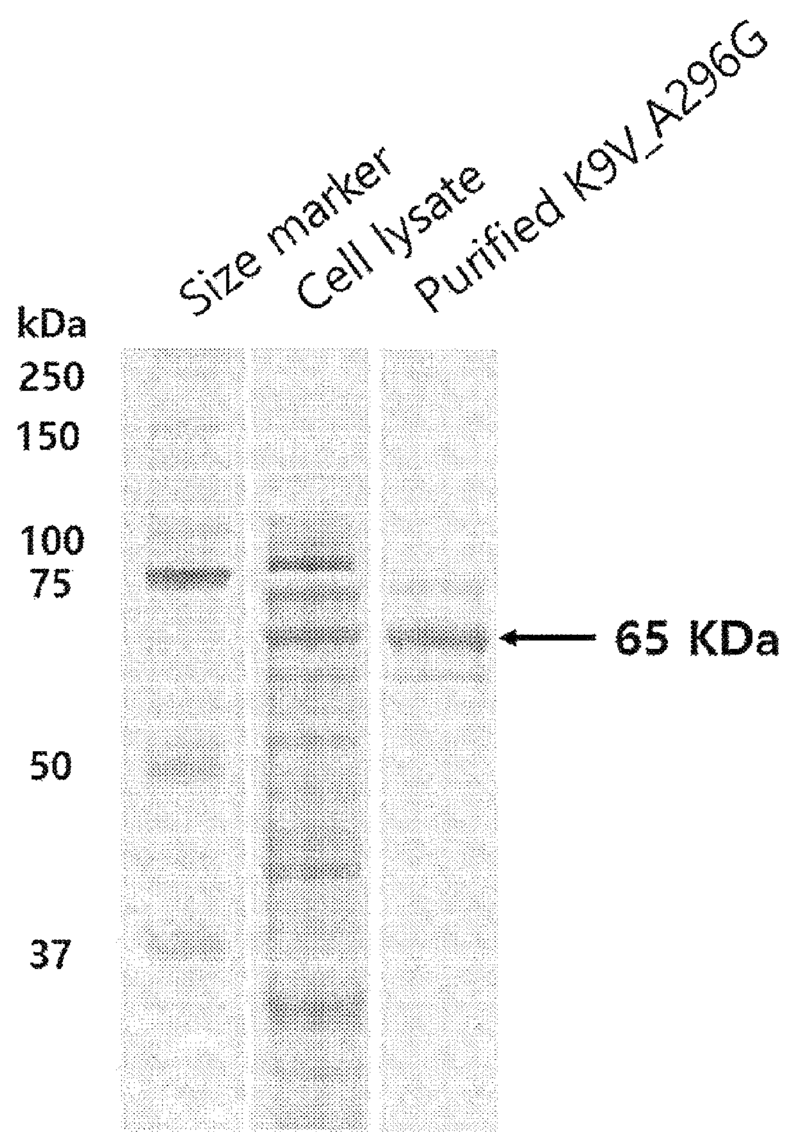
FIG. 1A illustrates a result of confirming the overexpression of a protein K9V_A296G having an amino acid sequence of SEQ ID NO: 1 by SDS-PAGE.

Hereinafter, the present invention will be described in detail.

1. Enzyme for Producing Multi-Hydroxy Derivatives of Polyunsaturated Fatty Acids An aspect of the present invention provides an enzyme for producing multi-hydroxy derivatives of polyunsaturated fatty acids.

An embodiment of the present invention provides an enzyme for producing a di-hydroxy derivative of polyunsaturated fatty acids and a gene encoding the enzyme for producing the di-hydroxy derivative of polyunsaturated fatty acids.

Another embodiment of the present invention provides an enzyme for producing a tri-hydroxy or tetra-hydroxy derivative of polyunsaturated fatty acids and a gene encoding the enzyme for producing the tri-hydroxy or tetra-hydroxy derivative of polyunsaturated fatty acids. The enzyme for producing the di-hydroxy derivative of polyunsaturated fatty acids of the present invention comprises an amino acid sequence of SEQ ID NO: 1 and the enzyme for producing the tri-hydroxy or tetra-hydroxy derivative of polyunsaturated fatty acids comprises an amino acid sequence of SEQ ID NO: 2. Within a range that does not affect the function of the enzyme for producing the di-hydroxy derivative of polyunsaturated fatty acids or the enzyme for producing the tri-hydroxy or tetra-hydroxy derivative of polyunsaturated fatty acids, the enzyme may be variants or fragments of amino acids having different sequences by deletion, insertion, substitution, or a combination of amino acid residues. Amino acid exchange has been known in the art at protein and peptide levels without changing entirely the activity of the enzyme for producing the di-hydroxy derivative of polyunsaturated fatty acids or the enzyme for producing the tri-hydroxy or tetra-hydroxy derivative of polyunsaturated fatty acids. In some cases, the amino acid exchange may be modified by phosphorylation, sulfation, acrylation, glycosylation, methylation, farnesylation, and the like. Accordingly, the present invention comprises a protein having an amino acid sequence substantially identical to the protein including the amino acid sequence of SEQ ID NO: 1 or SEQ ID NO: 2, and variants or active fragments thereof. The substantially identical proteins mean proteins having homology with the amino acid sequence of at least 90%, preferably at least 93%, and most preferably at least 95%, but are not limited thereto, and the proteins having homology of at least 90% with the amino acid sequence and identical enzyme activity are included in the scope of the present invention.

The gene of the enzyme for producing the di-hydroxy derivative of polyunsaturated fatty acids preferably consists of a nucleotide sequence of SEQ ID NO: 3, and the gene of the enzyme for producing the tri-hydroxy or tetra-hydroxy derivative of polyunsaturated fatty acids preferably consists of a nucleotide sequence of SEQ ID NO: 4. However, the genes encoding the enzyme for producing the di-hydroxy derivative of polyunsaturated fatty acids or the enzyme for producing the tri-hydroxy or tetra-hydroxy derivative of polyunsaturated fatty acids of the present invention, and variants or active fragments thereof may have various modifications made in an encoding region within a range without changing the amino acid sequence of the enzyme expressed from the encoding region and the variant or active fragment thereof. Various mutations may be made within a range without affecting the expression of the gene even in portions other than the encoding region, and such mutant genes are also included in the scope of the present invention. Accordingly, the present invention comprises a gene consisting of a nucleotide sequence substantially identical to the gene of SEQ ID NO: 3 or SEQ ID NO: 4 and fragments of the gene. The genes consisting of the substantially identical nucleotide sequences mean genes having sequence homology of 80% or more, preferably 90% or more, most preferably 95% or more, but are not limited thereto, and genes having sequence homology of 80% or more and having the identical enzyme activity of the encoded protein are included in the present invention. As such, the gene of the enzyme for producing the di-hydroxy derivative of polyunsaturated fatty acids of the present invention or the enzyme for producing the tri-hydroxy or tetra-hydroxy derivative of polyunsaturated fatty acids of the present invention may be mutated by substitution, deletion, and insertion of at least one nucleotide, or a combination thereof, as long as the gene encodes a protein having equivalent activity thereto, and these mutants are also included in the present invention.

The amino acid sequence of SEQ ID NO: 1 included in the enzyme for producing the di-hydroxy derivative is preferably encoded by a gene consisting of the nucleotide sequence of SEQ ID NO: 3, but the present invention is not limited thereto. The amino acid sequence of SEQ ID NO: 1 may also be encoded by a gene consisting of another nucleotide sequence substantially identical to the nucleotide sequence of SEQ ID NO: 3 as long as the amino acid sequence may encode the protein of the present invention having the identical amino acid sequence. These nucleotide sequences may be single-stranded or double-stranded, and may be DNA molecules or RNA molecules.

The amino acid sequence of SEQ ID NO: 2 included in the enzyme for producing the tri-hydroxy or tetra-hydroxy derivative of polyunsaturated fatty acids is preferably encoded by a gene consisting of the nucleotide sequence of SEQ ID NO: 4, but the present invention is not limited thereto. The amino acid sequence of SEQ ID NO: 2 may also be encoded by a gene consisting of another nucleotide sequence substantially identical to the nucleotide sequence of SEQ ID NO: 4 as long as the amino acid sequence may encode the protein of the present invention having the identical amino acid sequence. These nucleotide sequences may be single-stranded or double-stranded, and may be DNA molecules or RNA molecules.

Figure 1B:
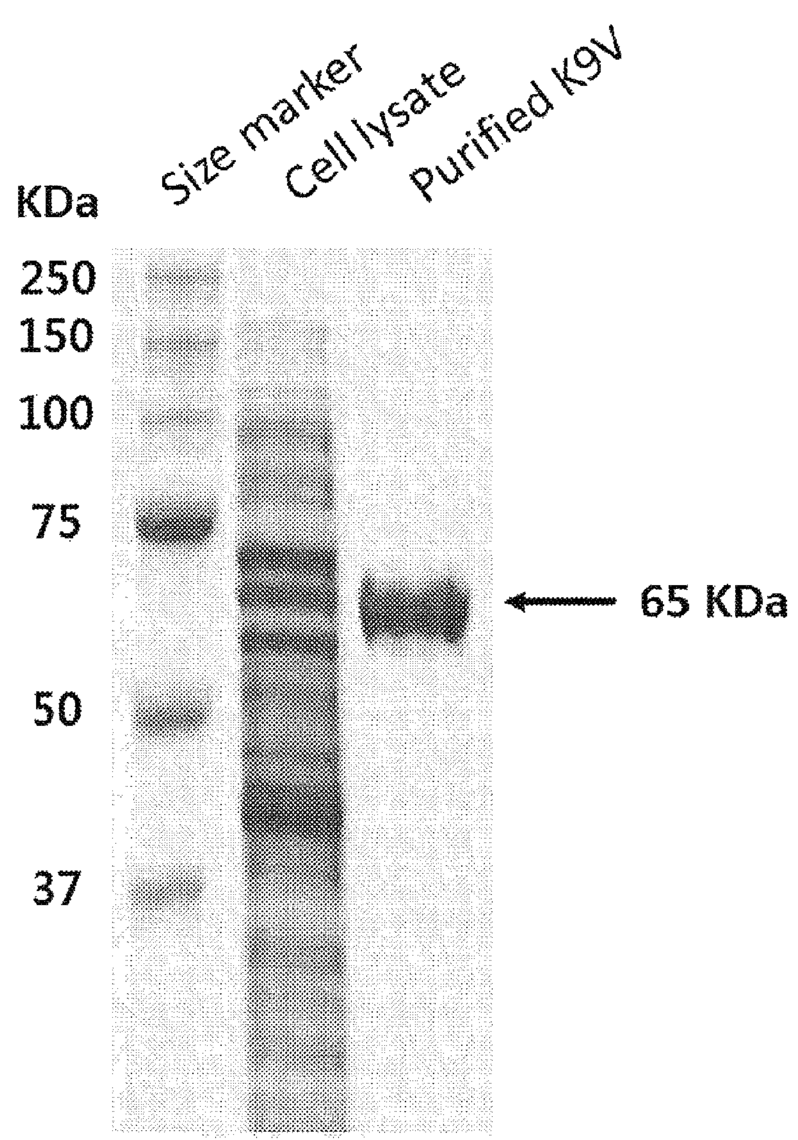
FIG. 1B illustrates a result of confirming the overexpression of a protein K9V having an amino acid sequence of SEQ ID NO: 2 by SDS-PAGE.

In a specific embodiment of the present invention, the present inventors had isolated and purified the protein having the amino acid sequence of SEQ ID NO: 1 and the protein having the amino acid sequence of SEQ ID NO: 2 to find the functions of the protein having the amino acid sequence of SEQ ID NO: 1 and the protein having the amino acid sequence of SEQ ID NO: 2 (see FIGS. 1A and 1B), and studied the activities thereof. As a result, the present inventors confirmed that the protein having the amino acid sequence of SEQ ID NO: 1 had the activity of an enzyme capable of producing the di-hydroxy derivative with two hydroxyl groups introduced into polyunsaturated fatty acids (see FIG. 3A) and the protein having the amino acid sequence of SEQ ID NO: 2 had the activity of an enzyme capable of producing the tri-hydroxy or tetra-hydroxy derivative of polyunsaturated fatty acids (see FIG. 3B).

2. Expression Vector and Transformant of Enzyme for Producing Multi-Hydroxy Derivatives of Polyunsaturated Fatty Acids Another aspect of the present invention provides a recombinant expression vector and a transformant introduced with the expression vector comprising a gene of the enzyme for producing the di-hydroxy derivative of polyunsaturated fatty acids of the present invention, or the gene of the enzyme for producing the tri-hydroxy or tetra-hydroxy derivative of polyunsaturated fatty acids of the present invention.

The recombinant expression vector of the present invention includes the gene of the enzyme for producing the di-hydroxy derivative of polyunsaturated fatty acids or the gene of the enzyme for producing the tri-hydroxy or tetra-hydroxy derivative of polyunsaturated fatty acids.

The expression vector includes a plasmid vector, a cosmid vector, a bacteriophage vector, a viral vector, and the like, but is not limited thereto.

The recombinant expression vector may combine expression regulatory sequences such as promoters, terminators, enhancers, etc., or sequences for secretion appropriately according to a type of host cell to produce the enzyme for producing the di-hydroxy derivative of polyunsaturated fatty acids of the present invention or the gene of the enzyme for producing the tri-hydroxy or tetra-hydroxy derivative of polyunsaturated fatty acids of the present invention.

The expression vector may further include a selection marker for selecting a host cell into which the vector has been introduced, and may include an origin of replication in the case of a replicable expression vector.

In addition, the recombinant expression vector may include a sequence for facilitating purification of the expressed protein, and specifically, may be linked with a gene encoding a tag for isolation and purification so as to be operable to the gene encoding the enzyme for producing the di-hydroxy derivative of polyunsaturated fatty acids of the present invention or the gene of the enzyme for producing the tri-hydroxy or tetra-hydroxy derivative of polyunsaturated fatty acids of the present invention. At this time, the tag for isolation and purification may use GST, poly-Arg, FLAG, histidine-tag, c-myc, or the like alone or may also use by sequentially linking two or more of the tags.

The gene encoding the enzyme for producing the di-hydroxy derivative of polyunsaturated fatty acids or the enzyme for producing the tri-hydroxy or tetra-hydroxy derivative of polyunsaturated fatty acids may be cloned through a restriction enzyme cleavage site. When a gene encoding a protein cleavage enzyme recognition site is used in the vector, the gene is linked with the gene of the enzyme for producing the di-hydroxy derivative of polyunsaturated fatty acids or the gene of the enzyme for producing the tri-hydroxy or tetra-hydroxy derivative of polyunsaturated fatty acids in frame. When the enzyme is obtained and then cleaved by the protein cleavage enzyme, an original type enzyme for producing the di-hydroxy derivative of polyunsaturated fatty acids or an original type enzyme for producing the tri-hydroxy or tetra-hydroxy derivative of polyunsaturated fatty acids may be produced.

In a specific embodiment of the present invention, the gene (the gene comprising the nucleotide sequence of SEQ ID NO: 3) of the enzyme for producing the di-hydroxy derivative of polyunsaturated fatty acids of the present invention or the gene (the gene comprising the nucleotide sequence of SEQ ID NO: 4) of the enzyme for producing the tri-hydroxy or tetra-hydroxy derivative of polyunsaturated fatty acids of the present invention are inserted to a plasmid vector pRL2 (Seo et al., *Biotechnol. Lett.,* 2009, 31:877-881), respectively, to prepare a recombinant cloning vector. In addition to the pRL2 used in the preparation of the cloning vector, various vectors for prokaryotic cells or eukaryotic cells (such as pPIC and pPICZ) are known, and thus, various expression vectors other than the vectors may be used depending on the purpose of expression.

The recombinant expression vector of the present invention may be effectively used as a vector including the gene of the enzyme for producing the di-hydroxy derivative of polyunsaturated fatty acids or the gene of the enzyme for producing the tri-hydroxy or tetra-hydroxy derivative of polyunsaturated fatty acids and capable of producing the gene of the enzyme.

The transformant of the present invention is introduced with the recombinant expression vector including the gene of the enzyme for producing the di-hydroxy derivative of polyunsaturated fatty acids or the gene of the enzyme for producing the tri-hydroxy or tetra-hydroxy derivative of polyunsaturated fatty acids.

The recombinant expression vector according to the present invention is transformed into any one suitable host cell selected from the group consisting of bacteria, yeast, *E. coli*, fungi, microalgae, algae, plant cells, and animal cells depending on the purpose of expression to prepare a transformant. For example, the host cell may be *E. coli* (*E. coli* BL21 (DE3), DH5α, etc.), yeast cells (*Saccharomyces* genus, *Pichia* genus, etc.), or the like. At this time, appropriate incubation methods and medium conditions, etc. may be easily selected by those skilled in the art from known techniques in the art depending on a type of host cell.

As a method for introducing the recombinant expression vector for the preparation of the transformant of the present invention, known techniques, that is, a heat shock method, an electric shock method, and the like may be used.

In a specific embodiment of the present invention, the transformant was prepared by transforming, into *E. coli*, the recombinant expression vector including the gene encoding the enzyme for producing the di-hydroxy derivative of polyunsaturated fatty acids of the present invention or the gene of the enzyme for producing the tri-hydroxy or tetra-hydroxy derivative of polyunsaturated fatty acids of the present invention by using *E. coli* as a host cell.

Since the protein expressed from the transformant is a protein of a novel sequence having the activity of the enzyme for producing the di-hydroxy derivative of polyunsaturated fatty acids or a protein of a novel sequence having the activity of the enzyme for producing the tri-hydroxy or tetra-hydroxy derivative of polyunsaturated fatty acids, the transformant is mass-incubated to express the gene, thereby facilitating the mass-production of the enzyme for producing the di-hydroxy derivative of polyunsaturated fatty acids or the enzyme for producing the tri-hydroxy or tetra-hydroxy derivative of polyunsaturated fatty acids.

3. Method for Producing Multi-Hydroxy Derivatives of Polyunsaturated Fatty Acids In Vitro Yet another aspect of the present invention provides a method for producing multi-hydroxy derivatives of polyunsaturated fatty acids in vitro, and more specifically, a method for producing a di-hydroxy derivative of polyunsaturated fatty acids in vitro and a method for producing a tri-hydroxy or tetra-hydroxy derivative of polyunsaturated fatty acids in vitro.

The method for producing the multi-hydroxy derivatives of polyunsaturated fatty acids in vitro of the present invention comprises reacting polyunsaturated fatty acids with the enzyme for producing the di-hydroxy derivative of polyunsaturated fatty acids or the enzyme for producing the tri-hydroxy or tetra-hydroxy derivative of polyunsaturated fatty acids described in the item of "1. Enzyme for producing multi-hydroxy derivatives of polyunsaturated fatty acids". The polyunsaturated fatty acids are fatty acids containing three or more double bonds between carbons, preferably omega-3 fatty acids, more preferably docosahexaenoic acid or eicosapentaenoic acid, but are not limited thereto. As described above, when the polyunsaturated fatty acids are used as a substrate of the enzyme for producing the di-hydroxy derivative, the substrate includes multiple double bonds into which hydroxyl groups may be introduced to achieve the production of the di-hydroxy derivative. In addition, when the polyunsaturated fatty acids are used as a substrate of the enzyme of producing the tri-hydroxy or tetra-hydroxy derivative, the substrate includes multiple double bonds into which hydroxyl groups may be introduced to achieve the production of the tri-hydroxy or tetra-hydroxy derivative.

The reacting of the polyunsaturated fatty acids with the enzyme for producing the di-hydroxy derivative of polyunsaturated fatty acids or the enzyme for producing the tri-hydroxy or tetra-hydroxy derivative of polyunsaturated fatty acids may be performed in a temperature range of 0° C. to 50° C., preferably in a temperature range of 15° C. to 35° C., but is not limited thereto. In addition, the reacting may be performed in a range of pH 4 to pH 10, preferably in a range of pH 7 to pH 9, but is not limited thereto. When the reacting is performed in the range of the temperature and pH, the activity of the enzyme for producing the di-hydroxy derivative of polyunsaturated fatty acids or the enzyme for producing the tri-hydroxy or tetra-hydroxy derivative of polyunsaturated fatty acids is maximized to more effectively produce the di-hydroxy derivative of polyunsaturated fatty acids or the tri-hydroxy or tetra-hydroxy derivative of polyunsaturated fatty acids.

Figure 8A:
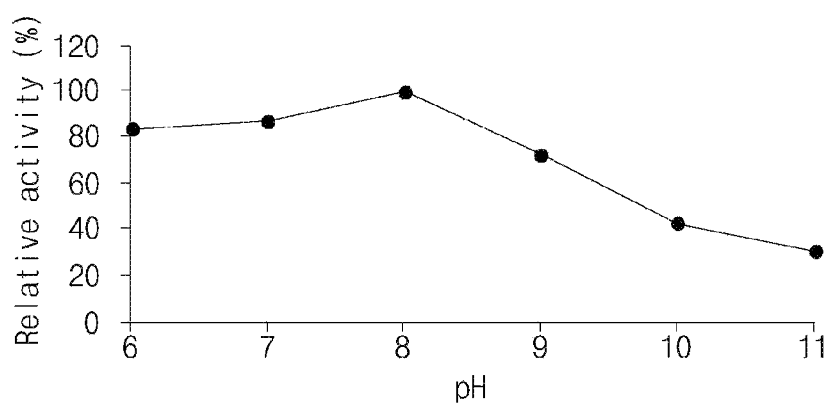
FIG. 8A is a graph showing a result of confirming an effect of a pH on the enzyme activity of a protein having an amino acid sequence of SEQ ID NO: 1
Figure 8B:
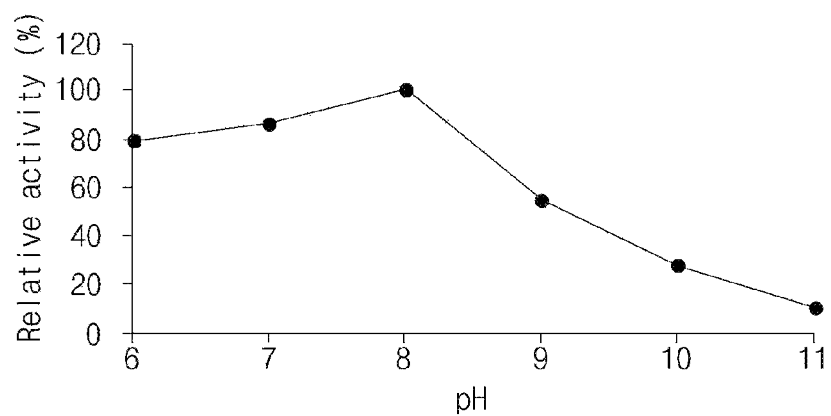
FIG. 8B is a graph showing a result of confirming an effect of a pH on the enzyme activity of a protein having an amino acid sequence of SEQ ID NO: 2.
Figure 9A:
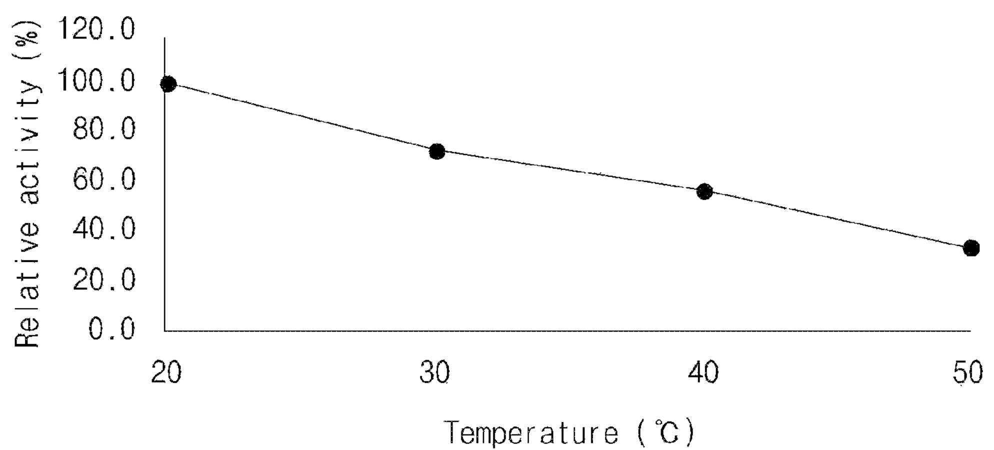
FIG. 9A is a graph showing a result of confirming an effect of a temperature on the enzyme activity of a protein having an amino acid sequence of SEQ ID NO: 1

In a specific embodiment of the present invention, it was confirmed that the protein having the amino acid sequence of SEQ ID NO: 1 having the activity as the enzyme for producing the di-hydroxy derivative of polyunsaturated fatty acids had optimal enzyme activity under conditions close to 20° C. and pH 8.0 (see FIGS. 8A and 9A). In addition, it was confirmed that the protein having the amino acid sequence of SEQ ID NO: 2 having the activity as the enzyme for producing the tri-hydroxy or tetra-hydroxy derivative of polyunsaturated fatty acids had optimal enzyme activity under conditions close to 30° C. and pH 8.0 (see FIGS. 8B and 9B).

The method for producing the multi-hydroxy derivatives of polyunsaturated fatty acids in vitro of the present invention further comprises recovering the di-hydroxy derivative of polyunsaturated fatty acids or the tri-hydroxy or tetra-hydroxy derivative of polyunsaturated fatty acids from a reaction product of the enzyme and the polyunsaturated fatty acids.

The recovering may be achieved by performing a method commonly performed in the art, such as centrifugation and filtration, and may be achieved by additionally performing a purification process in a general manner. For example, the purification process may be performed alone or in combination with techniques, such as solvent precipitation, dialysis, gel filtration, ion exchange, and chromatography such as reverse phase column chromatography.

4. Method for Producing Di-Hydroxy Derivative of Polyunsaturated Fatty Acids In Vivo Another aspect of the present invention provides a method for producing multi-hydroxy derivatives of polyunsaturated fatty acids in vivo, and more specifically, a method for producing a di-hydroxy derivative of polyunsaturated fatty acids in vivo and a method for producing a tri-hydroxy or tetra-hydroxy derivative of polyunsaturated fatty acids in vivo.

The method for producing the multi-hydroxy derivatives of polyunsaturated fatty acids in vivo of the present invention comprises incubating the transformant described in the item of "2. Expression vector and transformant of enzyme for producing multi-hydroxy derivatives of polyunsaturated fatty acids" in the presence of polyunsaturated fatty acids and isolating a di-hydroxy derivative of polyunsaturated fatty acids or a tri-hydroxy or tetra-hydroxy derivative of polyunsaturated fatty acids from the incubated culture medium.

In the transformant introduced with the recombinant expression vector containing the gene encoding the enzyme for producing the di-hydroxy derivative of polyunsaturated fatty acids or the tri-hydroxy or tetra-hydroxy derivative of polyunsaturated fatty acids, the enzyme for producing the di-hydroxy derivative of polyunsaturated fatty acids or the enzyme for producing the tri-hydroxy or tetra-hydroxy derivative of polyunsaturated fatty acids may be expressed. As a result, by using the same, the transformant is incubated in a culture medium containing polyunsaturated fatty acids as a substrate to produce the di-hydroxy derivative of polyunsaturated fatty acids or the tri-hydroxy or tetra-hydroxy derivative of polyunsaturated fatty acids without a separate process of isolating the enzyme.

With respect to the enzyme for producing the multi-hydroxy derivatives of polyunsaturated fatty acids present in the transformant, a detailed description thereof will be omitted by citing the description of the item of "1. Enzyme for producing multi-hydroxy derivatives of polyunsaturated fatty acids".

The incubation of the transformant may be performed according to an appropriate medium and incubation conditions known in the art. Those skilled in the art can easily adjust and use the medium and incubation conditions according to a type of transformant to be selected. The incubation method may include a batch type, a continuous type, a fed-batch type, or a combination thereof.

The medium may contain various carbon sources, nitrogen sources, and trace element ingredients.

The carbon sources may include, for example, carbohydrates such as glucose, sucrose, lactose, fructose, maltose, starch, and cellulose, fats such as soybean oil, sunflower oil, castor oil, and coconut oil, fatty acids such as palmitic acid, stearic acid, and linoleic acid, alcohols such as glycerol and ethanol, organic acids such as acetic acid, or combinations thereof. The incubation may be performed using glucose as the carbon source. The nitrogen sources may include organic nitrogen sources such as peptone, yeast extract, broth, malt extract, corn steep liquor (CSL), and soybean milk, inorganic nitrogen sources such as urea, ammonium sulfate, ammonium chloride, ammonium phosphate, ammonium carbonate, and ammonium nitrate, or combinations thereof. As a supply source of phosphorus, the medium may contain, for example, potassium dihydrogen phosphate, dipotassium hydrogen phosphate and sodium-containing salts corresponding thereto, and metal salts such as magnesium sulfate or iron sulfate.

In addition, amino acids, vitamins, suitable precursors, and the like may be included in the medium. The medium or individual ingredients may be added to the medium in a batch or continuous type.

In addition, during the incubation, production of bubbles may be inhibited by using an anti-foaming agent such as fatty acid polyclinic ester.

5. Novel Multi-Hydroxy Derivatives of Docosahexaenoic Acid

Another aspect of the present invention provides novel multi-hydroxy derivatives of docosahexaenoic acid.

In an embodiment of the present invention, the novel multi-hydroxy derivatives of docosahexaenoic acid may be a novel di-hydroxy derivative in which hydroxyl groups are introduced into positions 13 and 20 of docosahexaenoic acid, specifically, a compound having a chemical structure of Chemical Formula 1 below.

[Chemical Formula 1]

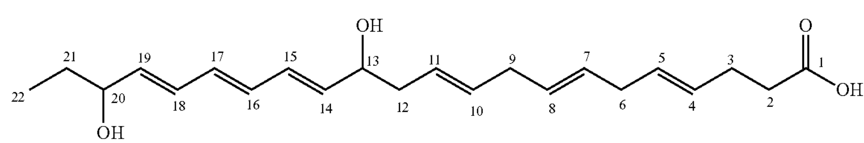

Particularly, the novel di-hydroxy derivative of docosahexaenoic acid may be obtained by reacting docosahexaenoic acid with an enzyme for producing the di-hydroxy derivative of polyunsaturated fatty acids of the present invention.

In another embodiment of the present invention, the other derivative of the novel multi-hydroxy derivatives of docosahexaenoic acid may be a novel tetra-hydroxy derivative in which hydroxyl groups are introduced into positions 7, 15, 16, and 17 of docosahexaenoic acid, specifically, a compound having a chemical structure of Chemical Formula 2 below.

[Chemical Formula 2]

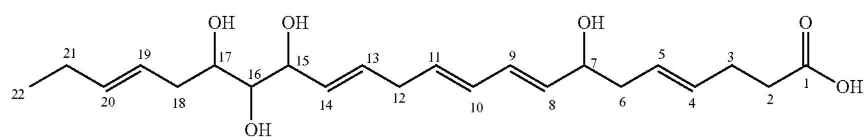

Particularly, the novel tetra-hydroxy derivative of docosahexaenoic acid may be obtained by reacting docosahexaenoic acid with an enzyme for producing the tri-hydroxy or tetra-hydroxy derivative of polyunsaturated fatty acids of the present invention.

6. Novel Multi-Hydroxy Derivatives of Docosapentaenoic Acid

Yet another aspect of the present invention provides novel multi-hydroxy derivatives of docosapentaenoic acid.

In an embodiment of the present invention, the novel multi-hydroxy derivatives of docosapentaenoic acid may be a novel di-hydroxy derivative in which hydroxyl groups are introduced into positions 7 and 15 of docosapentaenoic acid and epoxy groups are introduced into positions 16 and 17 of docosapentaenoic acid, specifically, a compound having a chemical structure of Chemical Formula 3 below.

[Chemical Formula 3]

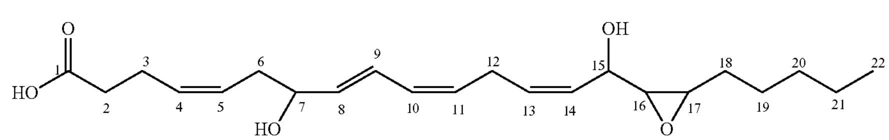

Particularly, the novel epoxide hydroxy derivative of docosapentaenoic acid may be obtained by reacting docosapentaenoic acid with the enzyme for producing the multi-hydroxy derivatives of polyunsaturated fatty acids of the present invention. Therefore, the enzyme for producing the multi-hydroxy derivatives of the present invention may be an enzyme for producing epoxide hydroxy.

7. Composition for Inhibiting Proliferation of Cancer Stem Cells

Meanwhile, still another aspect of the present invention provides a composition for inhibiting the proliferation of cancer stem cells.

In an embodiment of the present invention, the composition for inhibiting the proliferation of cancer stem cells comprises the di-hydroxy derivative of polyunsaturated fatty acids, as an active ingredient, obtained by reacting polyunsaturated fatty acids with the enzyme for producing the di-hydroxy derivative described in the item of "1. Enzyme for producing multi-hydroxy derivatives of polyunsaturated fatty acids". In addition, the composition for inhibiting the proliferation of cancer stem cells may further comprise a mono-hydroxy derivative, which is an intermediate product produced in the reaction process as described above.

In another embodiment of the present invention, the composition for inhibiting the proliferation of cancer stem cells comprises the tri-hydroxy derivative of polyunsaturated fatty acids, as an active ingredient, obtained by reacting polyunsaturated fatty acids with the enzyme for producing the tri-hydroxy or tetra-hydroxy derivative described in the item of "1. Enzyme for producing multi-hydroxy derivatives of polyunsaturated fatty acids". Further, the composition for inhibiting the proliferation of cancer stem cells may further comprise a tetra-hydroxy derivative which may be produced together with the mono-hydroxy derivative or di-hydroxy derivative, or the tri-hydroxy derivative which is an intermediate product produced in the reaction process as described above.

The polyunsaturated fatty acids are fatty acids containing three or more double bonds between carbons, preferably omega-3 fatty acids, more preferably docosahexaenoic acid or eicosapentaenoic acid, but are not limited thereto.

Among the multi-hydroxy derivatives of polyunsaturated fatty acids, particularly, the composition comprising the di-hydroxy derivative obtained by reacting the enzyme for producing the di-hydroxy derivative of polyunsaturated fatty acids of the present invention with polyunsaturated fatty acids, the tri-hydroxy derivative obtained by reacting the enzyme for producing the tri-hydroxy or tetra-hydroxy derivative of polyunsaturated fatty acids of the present invention with polyunsaturated fatty acids, or both the derivatives thereof has an effect of inhibiting the proliferation by acting specifically to cancer stem cells.

Figure 10A:
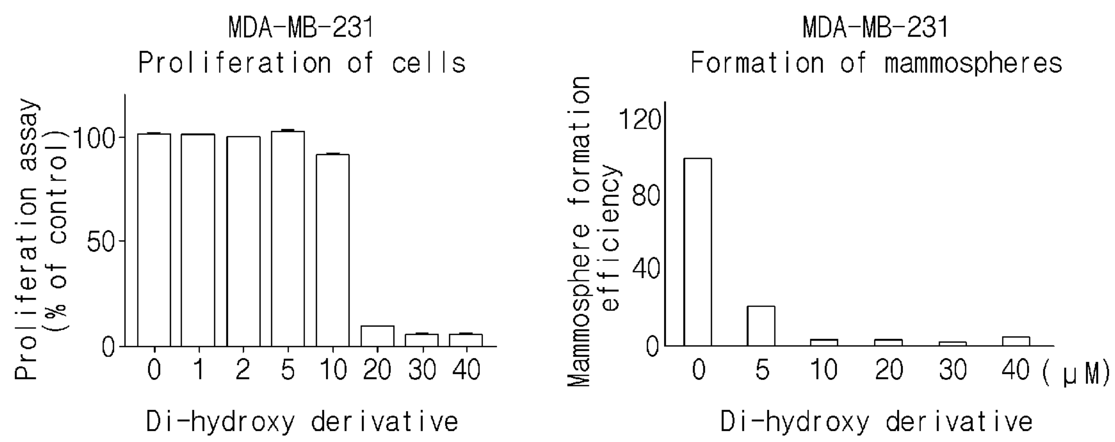
FIG. 10A illustrates a result of analyzing an effect of a di-hydroxy derivative produced by the protein having the amino acid sequence of SEQ ID NO: 1 on the proliferation of cancer cells and cancer stem cells.

In a specific embodiment of the present invention, the composition comprising the di-hydroxy derivative having the chemical structure of Chemical Formula 1 obtained by reacting docosahexaenoic acid with the protein having SEQ ID NO: 1 was treated to human breast cancer cells and cancer stem cells derived from human breast cancer, and as a result, it was confirmed that the proliferation thereof was inhibited specifically to the cancer stem cells derived from human breast cancer (see FIG. 10A). In addition, the composition comprising the tri-hydroxy derivative obtained by reacting docosahexaenoic acid with the protein having the amino acid sequence of SEQ ID NO: 2 was treated to human breast cancer cells and cancer stem cells derived from human breast cancer, and as a result, it was confirmed that the proliferation thereof was inhibited specifically to the cancer stem cells derived from human breast cancer (see FIG. 10B).

The 'cancer' generally refers to a mammalian physiological state characterized by unregulated cell growth, and refers to a state in which abnormality occurs in a regulating function of normal division, differentiation, and death of cells, and thus, the cells are abnormally overproliferated and infiltrated into surrounding tissues and organs to form a lump and destroy or transform the existing structure.

The "cancer stem cells" may be undifferentiated cells with the ability to differentiate into various cancer cells, wherein the cancer may be colorectal cancer including colon cancer and rectal cancer, breast cancer, uterine cancer, cervical cancer, ovarian cancer, prostate cancer, brain tumor, head and neck carcinoma, melanoma, myeloma, leukemia, lymphoma, gastric cancer, lung cancer, pancreatic cancer, liver cancer, esophageal cancer, small intestine cancer, cancer near the anus, fallopian tube carcinoma, endometrial carcinoma, vaginal carcinoma, vulvar carcinoma, Hodgkin's disease, bladder cancer, kidney cancer, ureter cancer, renal cell carcinoma, renal pelvic carcinoma, bone cancer, skin cancer, head cancer, neck cancer, skin melanoma, intraocular melanoma, endocrine cancer, thyroid cancer, parathyroid cancer, adrenal cancer, soft tissue sarcoma, urethral cancer, penile cancer, central nervous system (CNS) tumor, primary CNS lymphoma, spinal cord tumor, brainstem glioma, or pituitary adenoma, but is not particularly limited thereto. The cancer stem cells may be beast cancer stem cells which are undifferentiated cells with the ability to differentiate into beast cancer cells.

The 'inhibiting the proliferation of cancer stem cells' refers to including inhibiting the maintenance of cancer stem cells, inhibiting the malignance of cancer stem cells, and inhibiting the migration and invasion of cancer stem cells.

Meanwhile, the composition for inhibiting the proliferation of cancer stem cells may be used as a pharmaceutical composition or a food composition.

When the composition is used as the pharmaceutical composition, the composition may further comprise a pharmaceutically acceptable carrier or additive, in addition to the di-hydroxy derivative of polyunsaturated fatty acids.

The 'pharmaceutically acceptable' means that an object to be applied (prescribed) does not have toxicity beyond adaptable without inhibiting the activity of the active ingredient. The 'carrier' is defined as a compound that facilitates the addition of the compound into cells or tissues.

The di-hydroxy derivative of polyunsaturated fatty acids or the tri-hydroxy derivative of polyunsaturated fatty acids of the present invention may be administered alone or in combination with any convenient carrier, etc., and such a dose formulation may be a single-dose or repeat-dose formulation. The pharmaceutical composition may be a solid formulation or a liquid formulation. The solid formulation includes powders, granules, tablets, capsules, and suppositories, but is not limited thereto. The solid formulation may include a carrier, a flavoring agent, a binder, a preservative, a disintegrant, a lubricant, a filler, and the like, but is not limited thereto. The liquid formulation includes solutions such as water and propylene glycol solutions, suspensions, and emulsions, but is not limited thereto, and may be prepared by adding suitable coloring agents, flavoring agents, stabilizers, viscosifying agents, etc. For example, the powders may be prepared by simply mixing a suitable pharmaceutically acceptable carrier such as lactose, starch, microcrystalline cellulose, etc. with the di-hydroxy derivative of polyunsaturated fatty acids or the tri-hydroxy derivative of polyunsaturated fatty acids, which is the active ingredient of the present invention. The granules may be prepared by mixing the di-hydroxy derivative or the tri-hydroxy derivative of the present invention, a suitable pharmaceutically acceptable carrier, and a suitable pharmaceutically acceptable binder such as polyvinylpyrrolidone, hydroxypropyl cellulose, etc., and then using a wet granulation method using a solvent such as water, ethanol, and isopropanol or a dry granulation method using compressive force. In addition, the tablets may be prepared by mixing the granules with a suitable pharmaceutically acceptable lubricant such as magnesium stearate, and then tableting the mixture using a tablet press.

The di-hydroxy derivative of polyunsaturated fatty acids or the tri-hydroxy derivative of polyunsaturated fatty acids of the present invention may be administered with an oral agent, injections (e.g., intramuscular injection, intraperitoneal injection, intravenous injection, infusion, subcutaneous injection, and implant), an inhalation agent, a nasal administering agent, a vaginal agent, a rectal administering agent, a sublingual agent, a transdermal agent, a topical agent, or the like depending on a disease to be treated and a condition of a subject, but is not limited thereto. The derivatives may be formulated in a suitable dosage unit formulation including a pharmaceutically acceptable carrier, an additive, and a vehicle, which are conventionally used according to a route of administration and non-toxic.

The pharmaceutical composition of the present invention may be administered at a daily dose of about 0.0001 mg/kg to about 10 g/kg, and about 0.001 mg/kg to about 1 g/kg. However, the dose may vary depending on a degree of purification of the mixture, a patient's condition (age, sex, weight, etc.), and the severity of the condition being treated. If necessary, for convenience, the total daily dose may be divided and administered several times during a day.

When the composition of the present invention is used as a pharmaceutical composition, the di-hydroxy derivative of polyunsaturated fatty acids or the tri-hydroxy derivative of polyunsaturated fatty acids in the composition may be contained in a concentration of 30 μM or more, specifically 35 μM or more, more specifically 40 μM or more.

In addition, when the composition is used as a food composition, the composition may contain acceptable food supplement additives, and may further include suitable carriers, excipients, and diluents commonly used in the manufacture of food.

In the present invention, the food refers to a natural product or processed product containing one or more nutrients, and specifically, refers to a state that can be eaten directly through a certain processing process, and as a general meaning, is used as a meaning including all of various foods, functional foods, beverages, food additives, and beverage additives. Examples of the food include various foods, beverages, gum, tea, vitamin complexes, functional foods, and the like. In addition, the food of the present invention includes special nutritional foods (e.g., formulas, infant foods, etc.), processed meat products, fish meat products, tofu, muk, noodles (e.g., ramen, noodles, etc.), health supplement foods, seasoning foods (e.g., soy sauce, soybean paste, red pepper paste, mixed sauce, etc.), sauces, confectionery (e.g., snacks), dairy products (e.g., fermented milk, cheese, etc.), other processed foods, kimchi, salted foods (various kimchi, pickles, etc.), beverages (e.g., fruit, vegetable beverages, soy milk, fermented beverages, ice cream, etc.), natural seasonings (e.g., ramen soup, etc.), vitamin complexes, alcoholic beverages, liquors, and other health supplements, but is not limited thereto. The functional foods, beverages, food additives or beverage additives may be prepared by general preparation methods.

The term 'functional food' refers to food that is designed and processed to sufficiently express a body regulation function on the body with respect to biological defense rhythm control, disease prevention and recovery, etc. of a food group or food composition that has an added value to act and express the function of the corresponding food for a specific purpose by using physical, biochemical, and biotechnological methods, etc., and specifically, may be a health functional food.

The term 'health functional food' used in the present invention refers to food prepared and processed in the form of tablets, capsules, powders, granules, liquids and pills by using raw materials or ingredients having functionalities useful to the human body. Here, the 'function' refers to adjusting nutrients to the structure and function of the human body or to obtaining effects useful for health applications such as physiological action. The health functional food of the present invention may be prepared by methods which are commonly used in the art and may be prepared by adding raw materials and ingredients which are commonly added in the art in preparation. In addition, the formulation of the health functional food may also be prepared without limitation as long as the formulation is recognized as a health functional food. The food composition of the present invention may be prepared in various types of formulations, and unlike general drugs, the food composition has an advantage that there is no side effect that may occur when taking the drug in a long term by using the food as a raw material, and has excellent portability, but the health functional food of the present invention can be taken as supplements for enhancing an effect of inhibiting the growth of beast cancer stem cells.

In addition, the functional food may include sitologically acceptable food supplement additives, and may further include suitable carriers, excipients, and diluents commonly used in the manufacture of functional foods.

In addition, in the food composition, the di-hydroxy derivative of polyunsaturated fatty acids or the tri-hydroxy derivative of polyunsaturated fatty acids in the composition may be contained in a concentration of 30 μM or more, specifically 35 μM or more, more specifically 40 μM or more.

The food composition of the present invention may contain sweetening agents, flavoring agents, physiologically active ingredients, minerals, etc., in addition to the active ingredients. The sweetening agent may be used in an amount to give a suitable sweet taste of the food, and may be natural or synthetic. Specifically, when a natural sweetening agent is used, examples of the natural sweetening agent may include sugar sweetening agents such as corn syrup solids, honey, sucrose, fructose, lactose, and maltose. The flavoring agent may be used to improve taste or flavor, and both natural and synthetic flavoring agents may be used. Specifically, the natural flavoring agents are used. In the case of using the natural flavoring agents, the purpose of nutrient enhancement may be combined in addition to flavoring. The natural flavoring agents may be obtained from apples, lemons, tangerines, grapes, strawberries, peaches, and the like, or obtained from green tea leaves, solomon's seal, bamboo leaves, cinnamon, chrysanthemum leaves, jasmine, and the like. In addition, flavoring agents obtained from ginseng (red ginseng), bamboo shoots, aloe vera, and ginkgo may be used. The natural flavoring agents may be liquid concentrates or solid extracts. In some cases, the synthetic flavoring agents may be used, and the synthetic flavoring agents may use esters, alcohols, aldehydes, terpenes, and the like. As the physiologically active ingredients, catechins such as catechin, epicatechin, gallocatechin, and epigallocatechin, and vitamins such as retinol, ascorbic acid, tocopherol, calciferol, thiamine, and riboflavin may be used. As the minerals, calcium, magnesium, chromium, cobalt, copper, fluoride, germanium, iodine, iron, lithium, magnesium, manganese, molybdenum, phosphorus, potassium, selenium, silicon, sodium, sulfur, vanadium, zinc, and the like may be used.

In addition, the food composition of the present invention may contain a preservative, an emulsifier, an acidulant, a thickener, and the like, if necessary, in addition to the sweetening agent, and the like. These preservatives, emulsifiers, and the like are preferably added and used in a very trace amount as long as the application to be added may be achieved. The trace amount means a range of about 0.0005 wt % to about 0.5 wt % based on the total weight of the food composition when expressed numerically. Preservatives that may be used may include sodium calcium sorbate, sodium sorbate, potassium sorbate, calcium benzoate, sodium benzoate, potassium benzoate, ethylenediaminetetraacetic acid (EDTA), and the like. Examples of the emulsifier that may be used may include acacia gum, carboxymethylcellulose, xanthan gum, pectin, and the like. Examples of the acidulant that may be used may include citric acid, malic acid, fumaric acid, adipic acid, phosphoric acid, gluconic acid, tartaric acid, ascorbic acid, acetic acid, phosphoric acid, etc. These acidulants may be added so that the food composition has an appropriate acidity for the purpose of inhibiting the proliferation of microorganisms in addition to the purpose of enhancing taste. As the thickening agent that may be used, a suspending agent, a settling agent, a gel-forming agent, a swelling agent, and the like may be included.

Hereinafter, the present invention will be described in detail by Examples.

However, the following Examples are just illustrative of the present invention, and the contents of the present invention are not limited to the following Examples.

[Example 1] Preparation of Protein Comprising Amino Acid Sequence of SEQ ID NO: 1 or SEQ ID NO: 2

[1-1] Preparation of Vector for Expressing Protein

A nucleotide sequence of SEQ ID NO: 3 encoding each of amino acids of SEQ ID NO: 1 and a nucleotide sequence of SEQ ID NO: 4 encoding each of amino acids of SEQ ID NO: 2 were synthesized by requesting Bioneer Co., Ltd. Pre-denaturation was performed at 95° C. for 30 seconds using primer pairs of SEQ ID NOs: 5 and 6 using the synthesized nucleotide sequence as a template, and then PCR was performed by repeating cycles of reacting at 95° C. for 30 seconds, at 55° C. for 30 seconds, and at 68° C. for 5 minutes to amplify the gene of SEQ ID NO: 2.

TABLE 1

| Protein | | Primer nucleotide sequence (5'→3') | SEQ ID NO: |
|---|---|---|---|
| Amino acid of SEQ ID NO: 1 or 2 | Forward | ACTAGTATGGTAGACAATATGAAACCG | 5 |
| | Backward | ACGCGTGTGGTGGTGGTGGTGGTGCAT ACTGATGCTATTGATTACC | 6 |

PCR products containing the nucleotide sequence of SEQ ID NO: 3 and the nucleotide sequence of SEQ ID NO: 4 amplified as described above were inserted into a plasmid vector pRL2 (Seo et al., Biotechnol. Lett., 2009, 31:877-881), respectively, to prepare a recombinant expression vector. It was confirmed that the nucleotide sequence of SEQ ID NO: 3 and the nucleotide sequence of SEQ ID NO: 4 were properly inserted through nucleotide sequencing (Solgent).

[1-2] Expression and Purification of Protein

The recombinant expression vector prepared in Example [1-1] was transformed into *E. coli* DH5a, and the transformant was inoculated into 3 ml of an LB medium, and seed-incubated at 37° C. until the absorbance at 600 nm became 2.0. Then, a main incubation was performed for 24 hours by adding the seed-incubated culture medium to 500 ml of the LB medium.

A supernatant was separated by centrifuging the culture medium of the transformant in which overexpression was induced by the main incubation as described above, and cells of the transformant were lyzed from a pellet in which the supernatant was separated to obtain a cell lysate of the transformant.

As a result of performing SDS-PAGE on the cell lysate obtained as described above, as illustrated in FIGS. 1A and 1B, it was confirmed that a protein having an amino acid sequence of SEQ ID NO: 1 and a protein having an amino acid sequence of SEQ ID NO: 2 with sizes of about 65 KDa were overexpressed (see FIGS. 1A and 1B).

With respect to the cell lysate confirmed that the protein having the amino acid sequence of SEQ ID NO: 1 as described above was overexpressed, the protein having the amino acid sequence of SEQ ID NO: 1 was isolated and purified using Ni-NTA adsorption chromatography. With respect to the cell lysate confirmed that the protein having the amino acid sequence of SEQ ID NO: 2 as described above was overexpressed, the protein having the amino acid sequence of SEQ ID NO: 2 was isolated and purified using Ni-NTA adsorption chromatography.

[Example 2] Confirmation of Protein Activity

[2-1] Confirmation of Hydroxylation Activity

With respect to each of the protein having the amino acid sequence of SEQ ID NO: 1 and the protein having the amino acid sequence of SEQ ID NO: 2, purified and isolated in Example [1-2], 10 KU/ml of the protein and 100 μM of linoleic acid reacted with each other at pH 7 and room temperature for 30 minutes, a reaction product was reduced by adding 1 M of sodium borohydride so that the final concentration was 50 mM, and then the reaction was terminated by adding 5 μl/ml of acetic acid.

After the reaction product was purified using a solid phase cartridge (SPE, C18 500 mg), the types of compounds in the reaction product were analyzed using normal phase HPLC and chiral HPLC.

Specifically, the normal phase HPLC analysis for the compounds in the reaction product produced from the protein having the amino acid sequence of SEQ ID NO: 1 was performed by developing 20 ml of a mobile phase consisting of 94.8% n-heptane, 5% isopropanol, 0.1% acetic acid, and 0.1% 2,2-dimethoxypropane on a supelcosil LC-Diol column (Supelco, 25 cm×3 mm, 5 μm) at a flow rate of 0.5 ml/min for 40 minutes, and finally detecting the compounds in the reaction product using a diode array detector (DAD). The chiral-HPLC analysis was performed by developing 40 ml of a mobile phase consisting of 94.9% n-heptane, 5% isopropanol, 0.1% acetic acid, and 0.1% 2,2-dimethoxypropane on a supelcosil LC-Diol column (Supelco, 25 cm×3 mm, 5 μm) at a flow rate of 0.5 ml/min for 40 minutes, and finally detecting the compounds in the reaction product using a diode array detector (DAD).

In addition, the normal phase HPLC analysis for the compounds in the reaction product produced from the protein having the amino acid sequence of SEQ ID NO: 2 was performed by developing 20 ml of a mobile phase consisting of 95% n-heptane, 5% isopropanol, 0.1% acetic acid, and 0.1% 2,2-dimethoxypropane on a supelcosil LC-Diol column (Supelco, 25 cm×3 mm, 5 μm) at a flow rate of 0.5 ml/min for 40 minutes, and finally detecting the compounds in the reaction product using a diode array detector (DAD). The chiral-HPLC analysis was performed by developing 20 ml of a mobile phase consisting of 95% n-heptane, 5% isopropanol, 0.1% acetic acid, and 0.1% 2,2-dimethoxypropane on a supelcosil LC-Diol column (Supelco, 25 cm×3 mm, 5 μm) at a flow rate of 0.5 ml/min for 40 minutes, and finally detecting the compounds in the reaction product using a diode array detector (DAD).

Figure 2A:
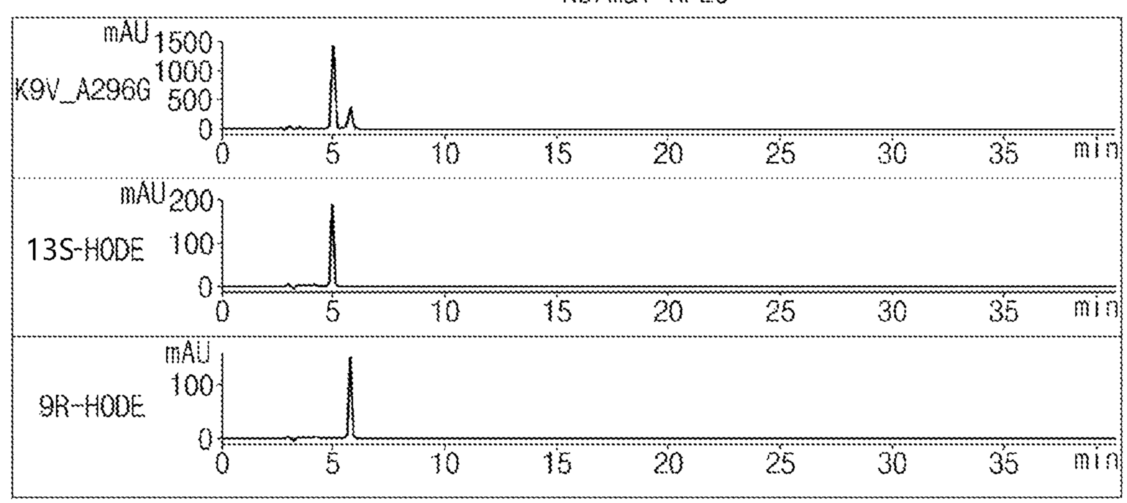
FIG. 2A illustrates results of performing normal phase HPLC analysis and chiral-HPLC analysis on a reaction product obtained by reacting a protein K9V_A296G having an amino acid sequence of SEQ ID NO: 1 with linoleic acid.
Figure 2A:
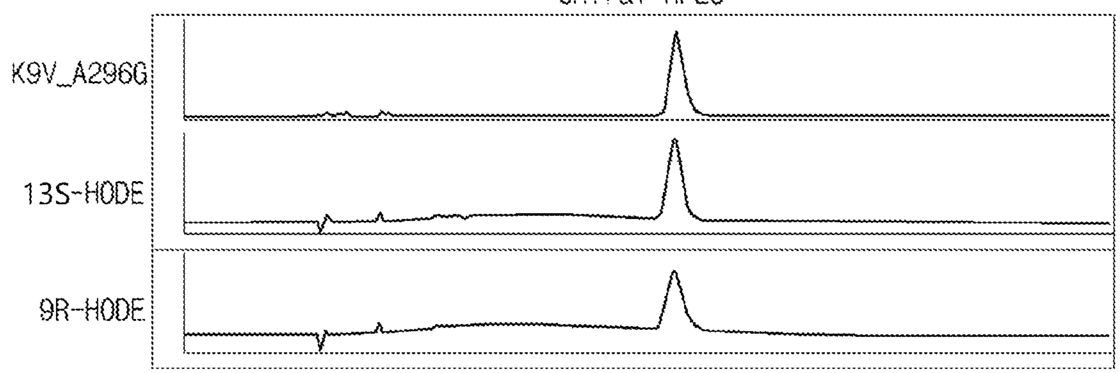
Figure 2B:
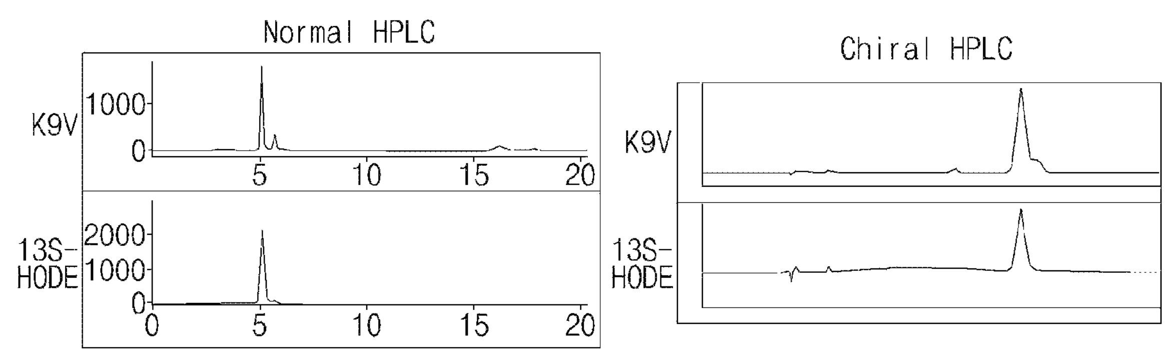
FIG. 2B illustrates results of performing normal phase HPLC analysis and chiral-HPLC analysis on a reaction product of a protein K9V having an amino acid sequence of SEQ ID NO: 2.

As a result, as illustrated in FIG. 2A, with respect to the reaction product produced from the protein having the amino acid sequence of SEQ ID NO: 1, in both the normal phase HPLC and the chiral HPLC, 9R-hydroxy-octadecadienoic acid (9R-HODE) and 13S-hydroxy-octadecadienoic acid (13S-HODE) were confirmed. In addition, as illustrated in FIG. 2B, with respect to the reaction product produced from the protein having the amino acid sequence of SEQ ID NO: 2, in both the normal phase HPLC and the chiral HPLC, the same peaks as 13S-hydroxy-octadodecadienoic acid (13S-HODE) were confirmed.

From the above results, it can be seen that the protein having the amino acid sequence of SEQ ID NO: 1 of the present invention has the activity to hydroxylate linoleic acid to 9R-hydroxy-octadecadienoic acid and 13S-hydroxy-octadecadienoic acid and the protein having the amino acid sequence of SEQ ID NO: 2 of the present invention has the activity to hydroxylate linoleic acid to 13S-hydroxy-octadodecadienoic acid.

[2-2] Confirmation of Activity of Producing Multi-Hydroxy Derivatives

With respect to the protein having the amino acid sequence of SEQ ID NO: 1 purified and isolated in Example [1-2], 2, 6, and 10 KU/ml of the protein and 100 μM of docosahexaenoic acid (DHA) reacted with each other at pH 7 and room temperature for 30 minutes, the reaction product was reduced by adding 1 M of sodium borohydride so that the final concentration was 50 mM, the reaction was terminated by adding 5 μl/ml of acetic acid, and then types of compounds in the reaction product were analyzed.

Figure 3A:
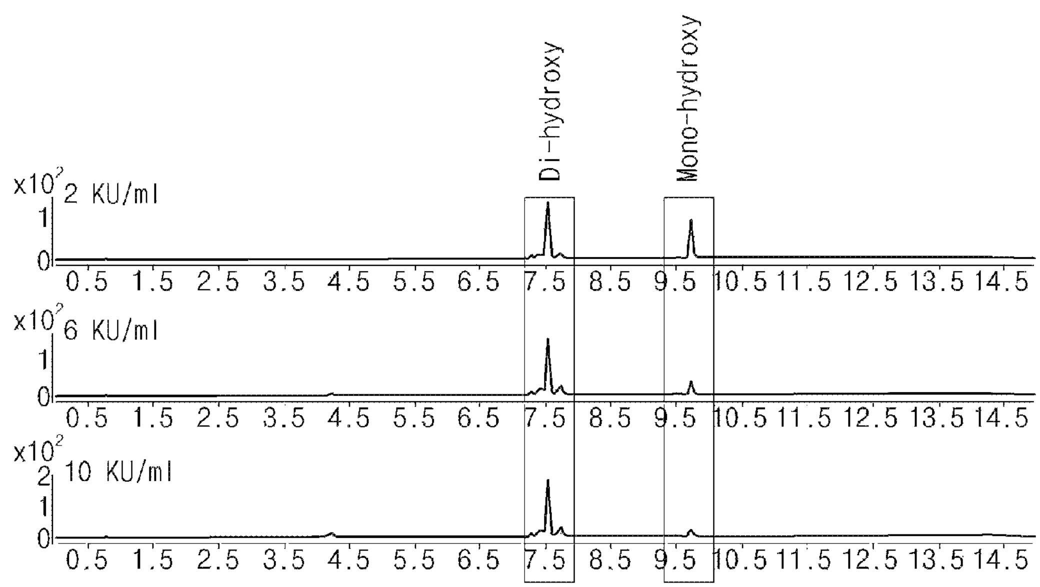
FIG. 3A illustrates a result of analyzing a hydroxy derivative present in a reaction product by performing reverse phase HPLC and mass spectrometry on the reaction product obtained by reacting a protein having an amino acid sequence of SEQ ID NO: 1 with docosahexaenoic acid.

As a result, as illustrated in FIG. 3A, it was confirmed that the protein having the amino acid sequence of SEQ ID NO: 1 may produce not only a mono-hydroxy derivative into which one hydroxyl group was introduced into DHA, but also a di-hydroxy derivative into which two hydroxyl groups were introduced.

Figure 4A:
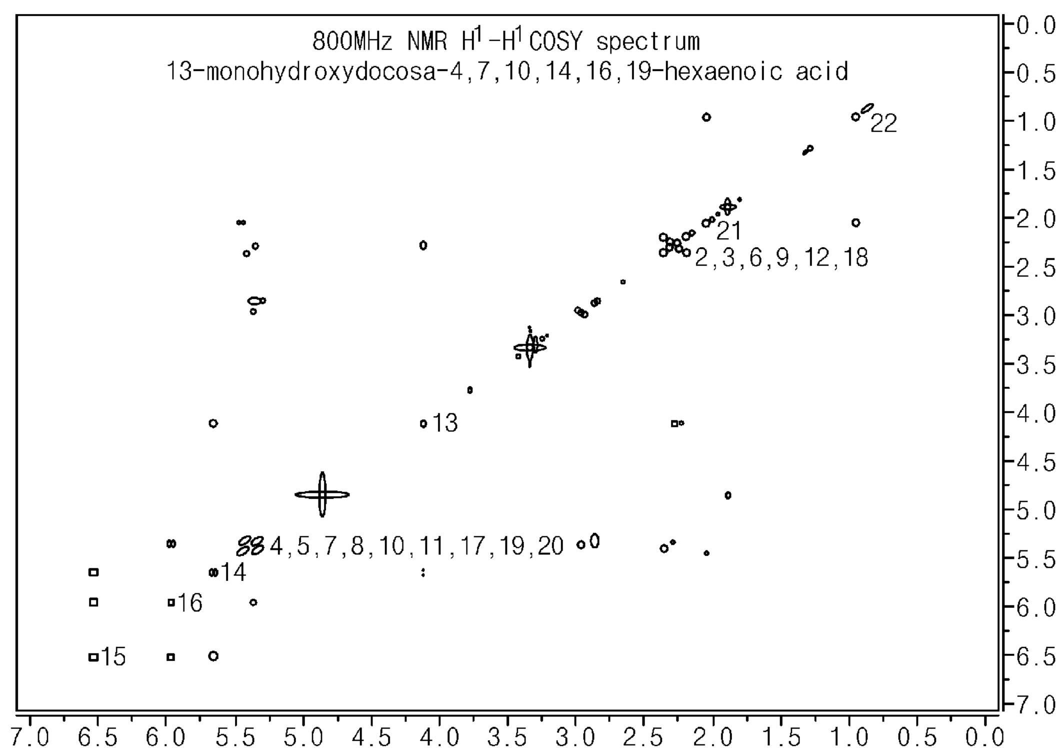
FIGS. 4A and 4B illustrate results of NMR analysis of a reaction product obtained by reacting a protein having an amino acid sequence of SEQ ID NO: 1 with docosahexaenoic acid.
Figure 4B:
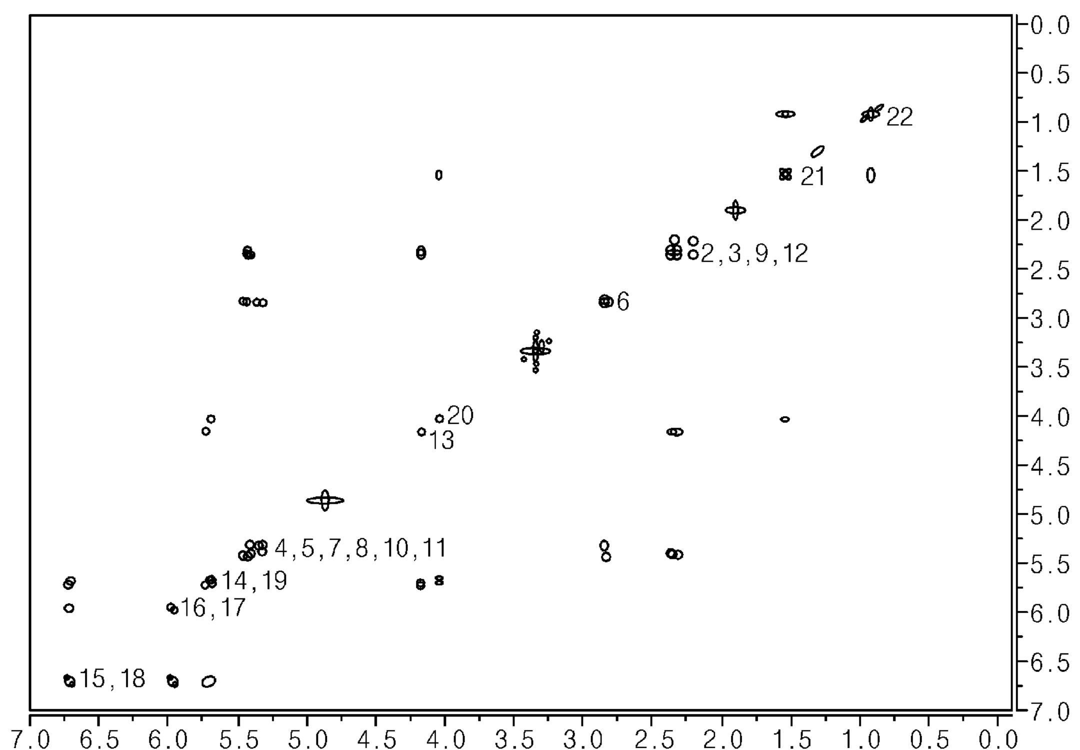

In addition, NMR analysis was performed on the reaction products. Specifically, the mono- or di-hydroxy derivative converted from docosahexaenoic acid is an organic substance consisting of C, O, and H, and 800 MHz NMR (Bruker) was used to analyze a structure by measuring chemical shift values between these chemical species. As a solvent for NMR measurement, D4-methanol in which hydrogen was substituted with deuterium was used, and the measurement was performed at an absolute temperature of 298 K. Hydrogen and carbons constituting the mono- or di-hydroxy derivative were measured by using 1D NMR ($^{1}$H, $^{13}$C) and 2D NMR ($^{1}$H-$^{1}$H COSY, Edited-QC, HMBC, TOCSY, ROESY) (FIGS. 4A and 4B).

Figure 5A:
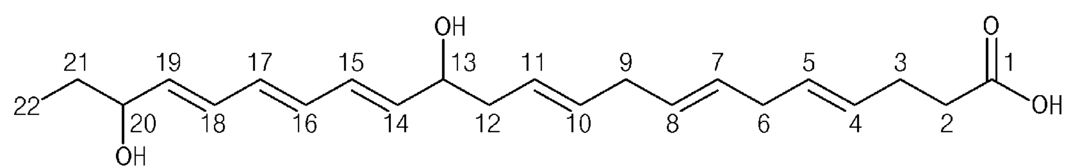
FIGS. 5A and 5B illustrate chemical structures of derivatives confirmed by the results of NMR analysis on a reaction product obtained by reacting a protein having an amino acid sequence of SEQ ID NO: 1 with docosahexaenoic acid, wherein the FIG. 5A illustrates a chemical structural formula of a di-hydroxy derivative produced by the protein having the amino acid sequence of SEQ ID NO: 1
Figure 5B:
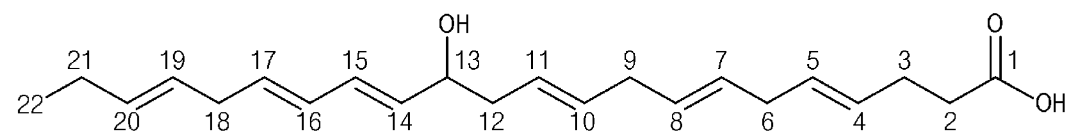

As a result, as illustrated in FIGS. 5A and 5B, it was confirmed that the protein having the amino acid sequence of SEQ ID NO: 1 introduced hydroxyl groups at positions 13 and 20 of DHA to produce a di-hydroxy derivative (FIG. 5A). In this process, it was confirmed that as an intermediate product, a mono-hydroxy derivative having a hydroxyl group introduced into position 13 was also present (FIG. 5B).

With respect to the protein having the amino acid sequence of SEQ ID NO: 2 purified and isolated in Example [1-2], 2, 6, and 10 KU/ml of the protein and 100 μM of docosahexaenoic acid (DHA) reacted with each other at pH 7 and room temperature for 30 minutes, the reaction product was reduced by adding 1 M of sodium borohydride so that the final concentration was 50 mM, the reaction was terminated by adding 5 μl/ml of acetic acid, and then types of compounds in the reaction product were analyzed.

Figure 3B:
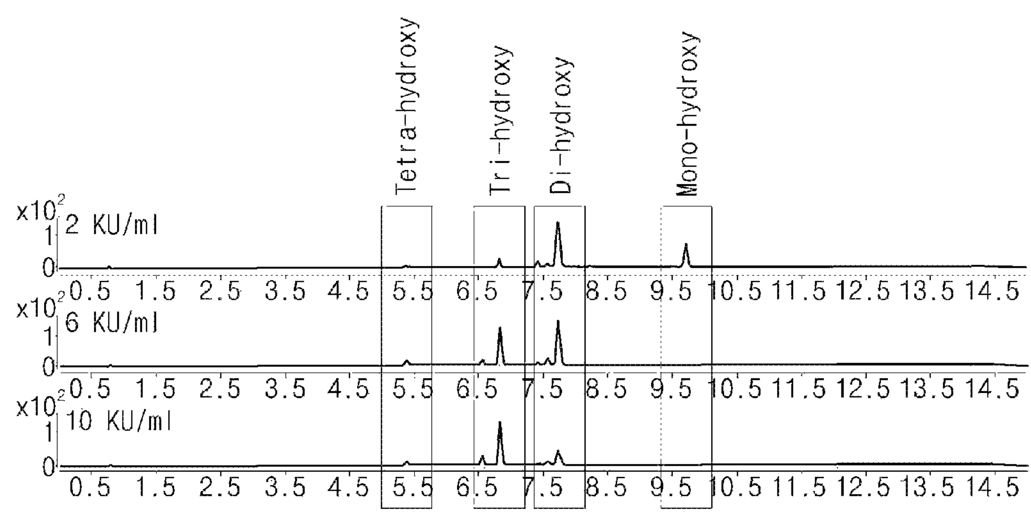
FIG. 3B illustrates a result of analyzing a hydroxy derivative present in a reaction product by performing reverse phase HPLC and mass spectrometry on the reaction product obtained by reacting a protein having an amino acid sequence of SEQ ID NO: 2 with docosahexaenoic acid.

As a result, as illustrated in FIG. 3B, it was confirmed that the protein having the amino acid sequence of SEQ ID NO: 2 may produce not only a mono-hydroxy derivative introduced with one hydroxyl group into DHA and a di-hydroxy derivative introduced with two hydroxyl groups, but also a tri-hydroxy derivative introduced with three hydroxyl groups and a tetra-hydroxy derivative introduced with four hydroxyl groups.

Figure 4C:
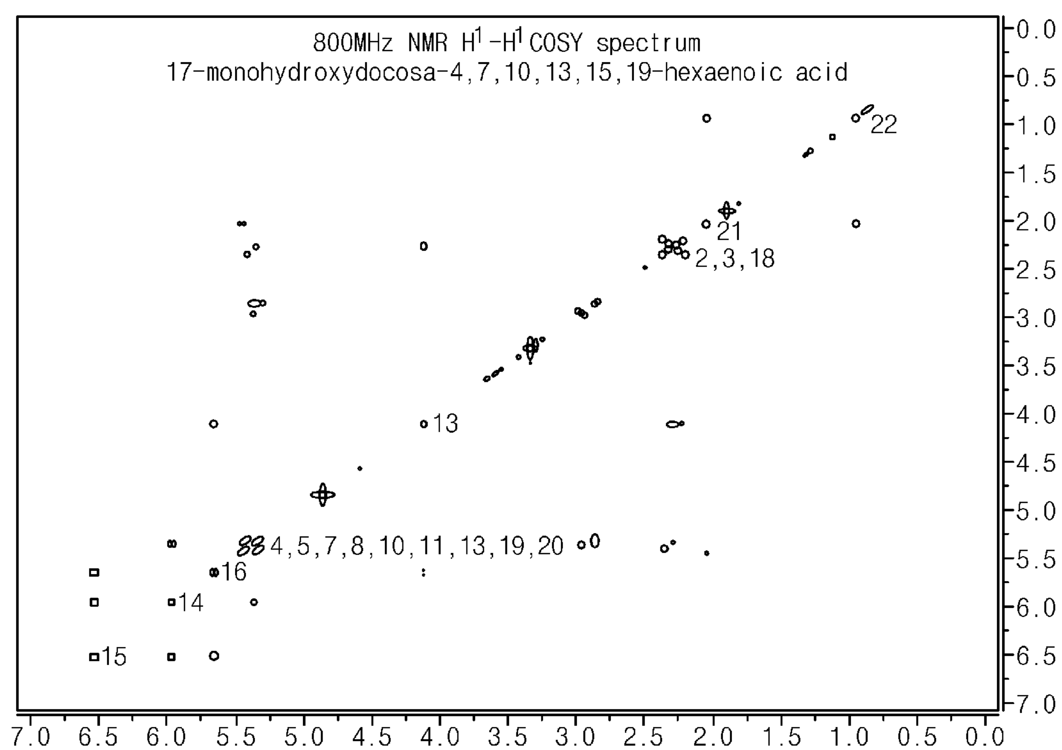
FIG. 4C to 4E illustrate results of NMR analysis of a reaction product obtained by reacting a protein having an amino acid sequence of SEQ ID NO: 2 with docosahexaenoic acid. In addition.
Figure 4D:
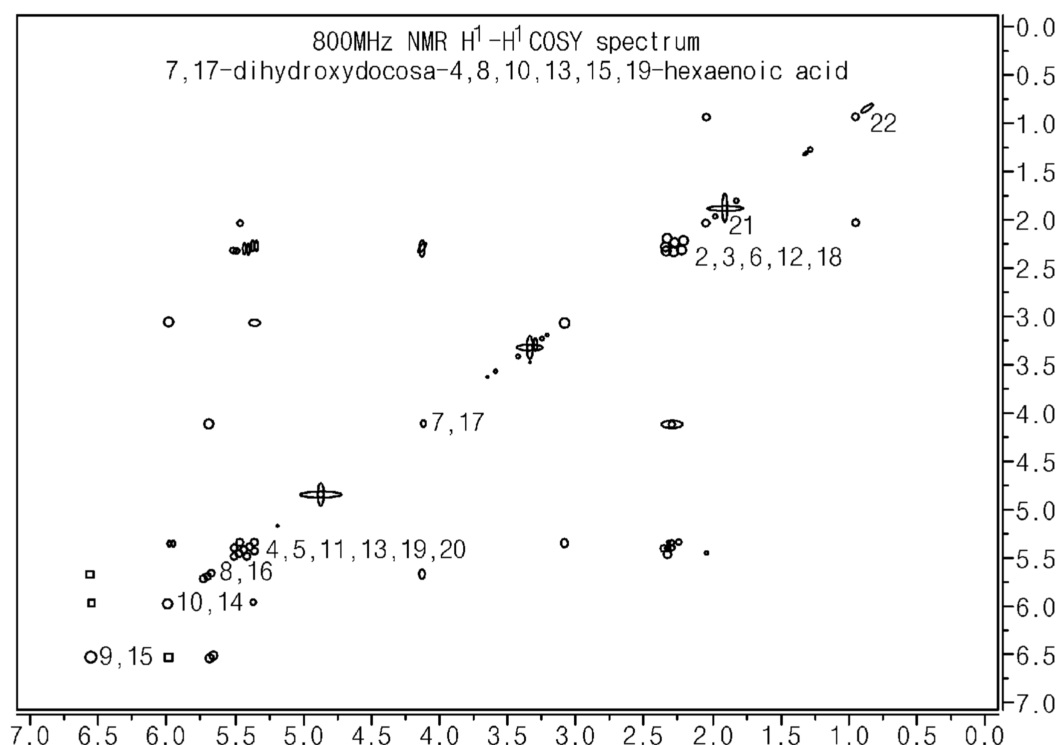
Figure 4E:
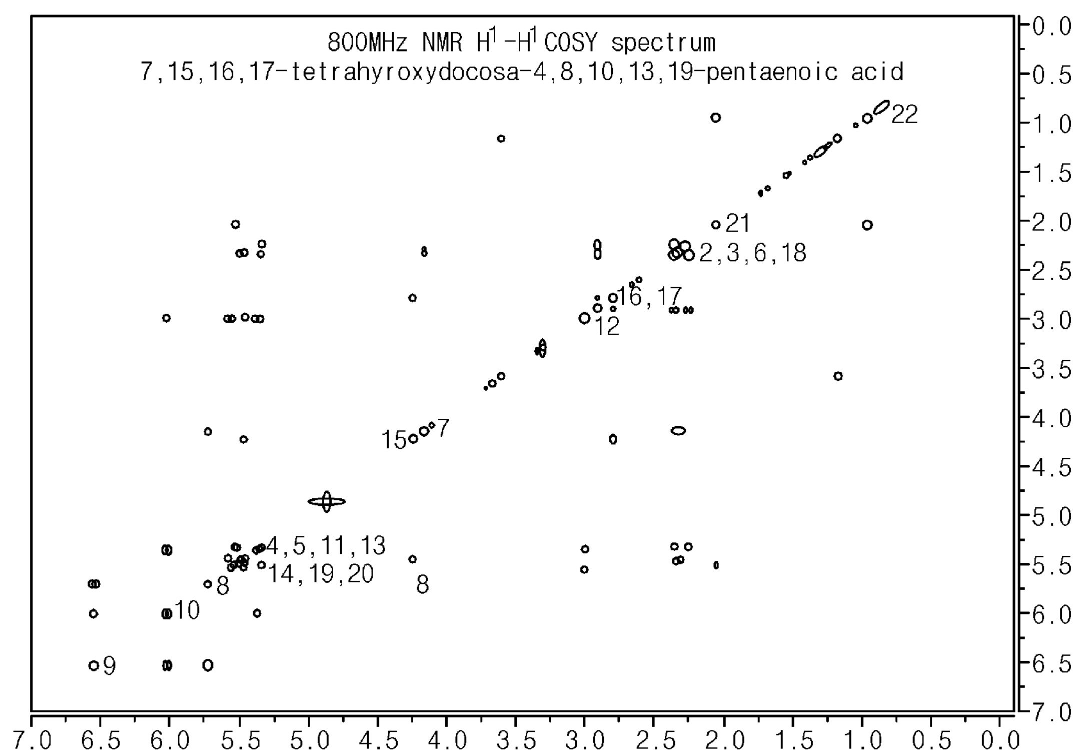

In addition, NMR analysis was performed on the reaction products. Specifically, the mono-, di-, tri-, or tetra-hydroxy derivative converted from docosahexaenoic acid is an organic substance consisting of C, O, and H, and 800 MHz NMR (Bruker) was used to analyze a structure by measuring chemical shift values between these chemical species. As a solvent for NMR measurement, D4-methanol in which hydrogen was substituted with deuterium was used, and the measurement was performed at an absolute temperature of 298 K. Hydrogen and carbons constituting the mono-, di- or tetra-hydroxy derivative were measured by using 1D NMR ($^{1}$H, $^{13}$C) and 2D NMR ($^{1}$H-$^{1}$H COSY, Edited-QC, HMBC, TOCSY, ROESY) (FIGS. 4C to 4E).

Figure 5C:
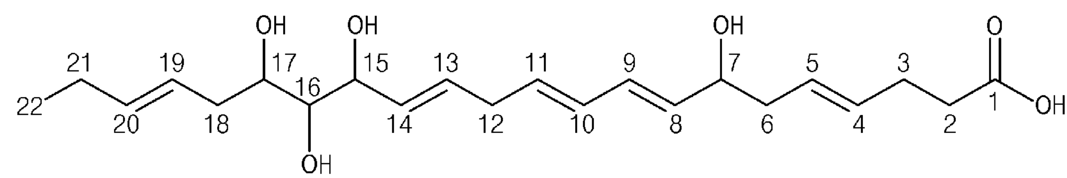
Figure 5D:
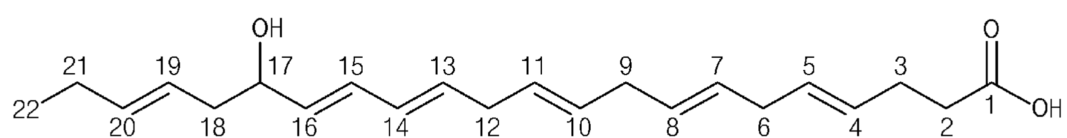
Figure 5E:
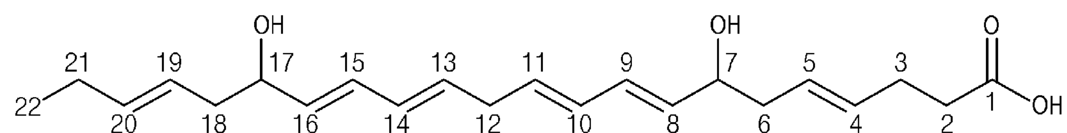

As a result, as illustrated in FIGS. 5C to 5E, it was confirmed that the protein having the amino acid sequence of SEQ ID NO: 2 had hydroxyl groups introduced into positions 7, 15, 16 and 17 of DHA to produce a tetra-hydroxy derivative (FIG. 5C). In this process, it was confirmed that as intermediate products, a mono-hydroxy derivative having a hydroxyl group introduced into position 17 (FIG. 5D) and a di-hydroxy derivative having hydroxyl groups introduced into positions 7 and 17 (FIG. 5E) were also present.

Figure 6:
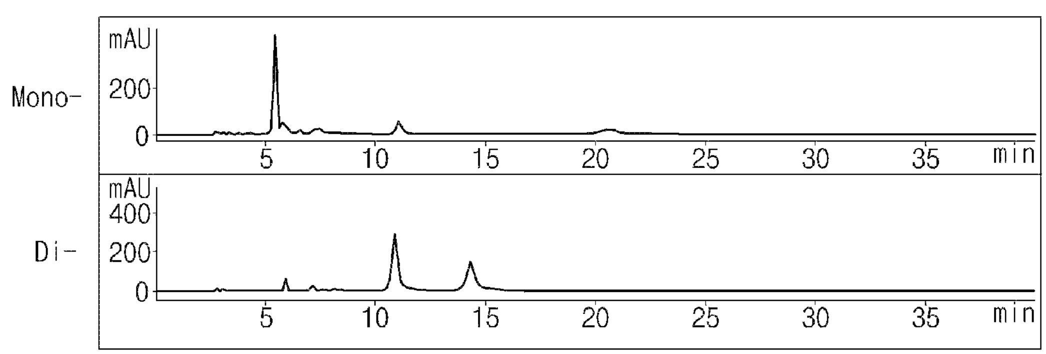
FIG. 6 illustrates a result of analyzing hydroxy derivatives present in a reaction product by performing normal phase HPLC analysis on the reaction product obtained by reacting a soybean 15-LOX enzyme as a control with docosahexaenoic acid.

On the contrary, in the case of soybean 15LOX, as illustrated in FIG. 6, it was confirmed that only one or two hydroxyl groups may be introduced into docosahexaenoic acid, and derivatives introduced with three or four hydroxyl groups were not produced.

With respect to the protein having the amino acid sequence of SEQ ID NO: 1 purified and isolated in Example [1-2], 2, 6, and 10 KU/ml of the protein and 100 μM of docosapentaenoic acid (DPA) reacted with each other at pH 7 and room temperature for 30 minutes, the reaction product was reduced by adding 1 M of sodium borohydride so that the final concentration was 50 mM, the reaction was terminated by adding 5 μl/ml of acetic acid, and then types of compounds in the reaction product were analyzed. As a result, like DHA, it was confirmed that an epoxide hydroxy derivative was produced.

Figure 4F:
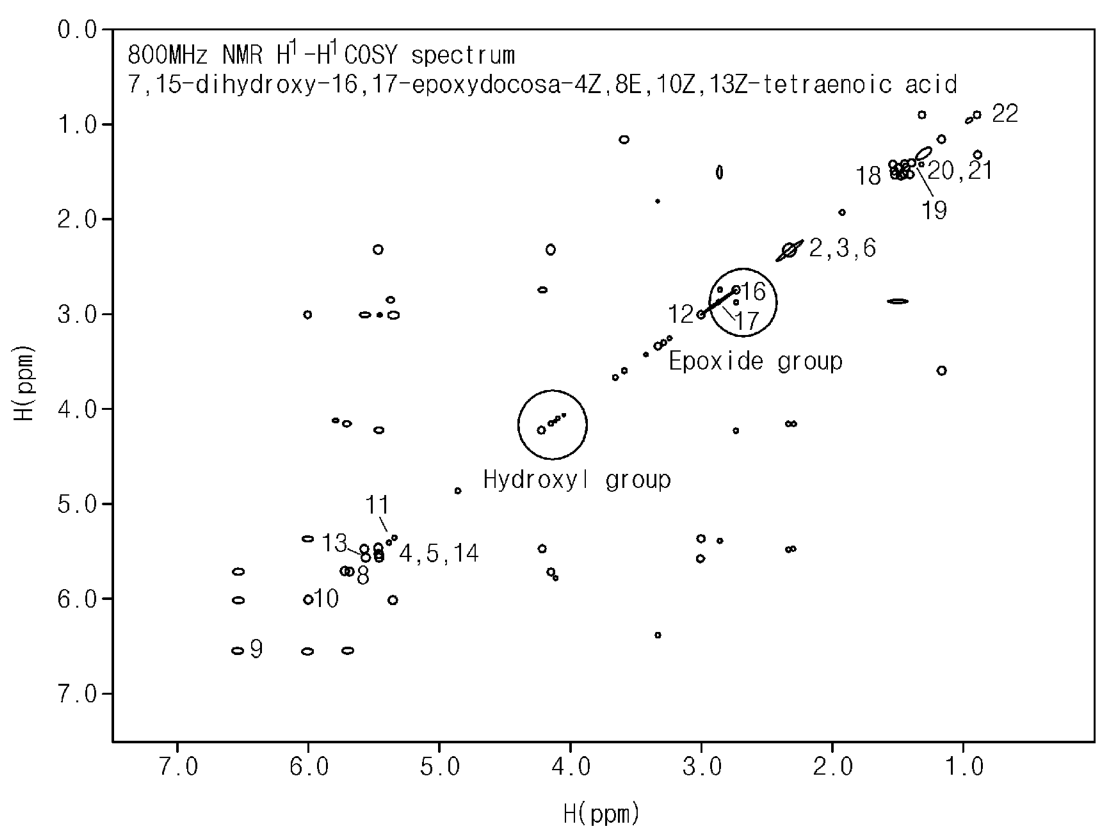
FIG. 4F illustrates a result of NMR analysis on a reaction product obtained by reacting a protein having an amino acid sequence of SEQ ID NO: 1 with docosapentaenoic acid.

In addition, NMR analysis was performed on the reaction product. Specifically, the epoxide hydroxy derivative converted from docosapentaenoic acid is an organic substance consisting of C, O, and H, and 800 MHz NMR (Bruker) analysis was performed to determine an exact structure by measuring chemical shift values between these species. For NMR analysis, a solvent of the reaction product used D4-methanol in which hydrogen was substituted with deuterium. By using 1D NMR ($^{1}$H, $^{13}$C) and 2D NMR ($^{1}$H-$^{1}$H COSY, 1H-1H TOCSY, 1H-13C Edited-HSQC, 1H-13C HMBC), hydrogen and carbons constituting the hydroxy derivatives were measured at an absolute temperature of 298 K (FIG. 4F).

Figure 5F:
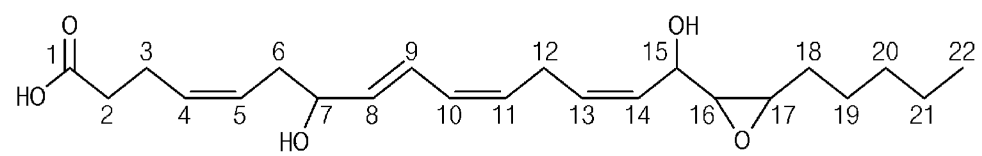
FIG. 5F illustrates a chemical structure of an epoxide hydroxy derivative produced by reacting a protein having an amino acid sequence of SEQ ID NO: 1 with docosapentaenoic acid.

As a result, it was confirmed that the protein having the amino acid sequence of SEQ ID NO: 1 produced an epoxide dihydroxy derivative in which hydroxyl groups were introduced into positions 7 and 15 of DPA, and epoxy groups were introduced into positions 16 and 17 of DPA (FIG. 5F).

[Example 3] Amino Acid Sequence Analysis of Protein

With respect to the protein having the amino acid sequence of SEQ ID NO: 1 and the amino acid sequence of SEQ ID NO: 2 in which the activity as the enzyme in Example 2 was confirmed, as compared to human 12LOX, human 15LOX, human 5LOX, potato LOX, soybean 15LOX and red algae PhLOX, which were lipoxygenase enzymes having similar activities, homology analysis and system analysis of amino acid sequences were performed.

Figure 7:
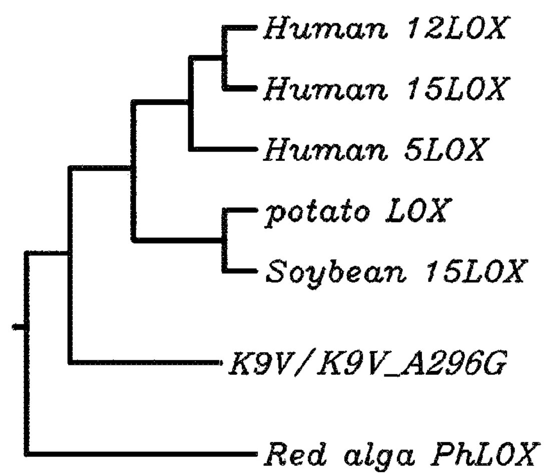
FIG. 7 illustrates a result of analyzing system analysis, based on results of analyzing homology of amino acid sequences with human 5LOX, human 12LOX, human 15LOX, soybean 15LOX, potato LOX, and red algae PhLOX, which are lipoxygenase enzymes with similar activity, with respect to a protein K9V_A296G having an amino acid sequence of SEQ ID NO: 1 and a protein K9V having an amino acid sequence of SEQ ID NO: 2.

As a result, it was confirmed that the protein having the amino acid sequence of SEQ ID NO: 1 had the sequence homology of 21% with soybean 15LOX; 26% of human 5LOX; 23% of human 12LOX; 25% of human 15LOX; 23% of potato LOX; and 21% of red algae PhLOX. In addition, it was confirmed that the protein having the amino acid sequence of SEQ ID NO: 2 had the sequence homology of 21% with soybean 15LOX; 26% of human 5LOX; 25% of human 15LOX; 23% of potato LOX; and 21% of red algae PhLOX. In addition, as a result of the system analysis based thereon, the protein having the amino acid sequence of SEQ ID NO: 1 and the protein having the amino acid sequence of SEQ ID NO: 2 were classified as a completely different system from human 15LOX, human 5LOX, potato LOX, soybean 15LOX and red algae PhLOX as illustrated in FIG. 7.

In addition, in the protein having the amino acid sequence of SEQ ID NO: 1, it was confirmed that an N-terminal region for binding to the membrane lipid was deleted, while a C-terminal region had high similarity to general lipoxygenase. It was confirmed that residues binding to iron ions, such as His, His, His and Asn/Ser, and terminal amino acids were present, and Ala, which was closely associated with the hydroxylation properties of the enzyme, was present.

In addition, as a result of analyzing a secondary structure of the protein having the amino acid sequence of SEQ ID NO: 1, it was confirmed that α-helixes, extended strands, and random coils existed at ratios shown in Table 2 below, respectively.

TABLE 2

| Enzyme | Secondary structure | Ratio |
|---|---|---|
| Protein having amino acid sequence of SEQ ID NO: 1 | α-helixes | 41.68% |
| | Extended strands | 6.66% |
| | Random coils | 51.66% |

On the other hand, in the protein having the amino acid sequence of SEQ ID NO: 2, it was confirmed that the N-terminal region binding to the membrane lipid was deleted. On the other hand, in the C-terminal region, it was confirmed that residues binding to iron ions, such as His, His, His, Asn/Ser, and terminal amino acids were present, and Ala, which was closely associated with the hydroxylation properties of the enzyme, was present. In addition, as a result of analyzing a secondary structure of the protein having the amino acid sequence of SEQ ID NO: 2, it was confirmed that α-helixes, extended strands, and random coils existed at ratios shown in Table 3 below, respectively.

TABLE 3

| Enzyme | Secondary structure | Ratio |
|---|---|---|
| Protein having amino acid sequence of SEQ ID NO: 2 | α-helixes | 41.68% |
| | Extended strands | 6.66% |
| | Random coils | 51.66% |

[Example 4] Confirmation of Conditions Affecting Enzyme Activity of Protein

Conditions that affected the enzyme activity of each protein were confirmed with respect to the protein having the amino acid sequence of SEQ ID NO: 1 and the protein having the amino acid sequence of SEQ ID NO: 2, purified and isolated in Example [1-2].

[4-1] Effect of pH

In order to confirm an effect of a pH, 10 KU/ml of the protein having the amino acid sequence of SEQ ID NO: 1 purified and isolated in Example [1-2] and 100 μM of linoleic acid reacted with each other at pH 7 to pH 11 and a temperature of 25° C. for 30 minutes, a reaction product was reduced by adding 1 M of sodium borohydride so that the final concentration became 50 mM to reduce, and then the reaction was completed by adding 5 μl/ml of acetic acid. At this time, 50 mM of a sodium phosphate buffer in the case of pH 7.0, 50 mM of a Tris-HCl buffer in the case of pH 8.0, and 50 mM of a sodium borate buffer in the case of pH 9.0 to pH 11.0 were used, respectively.

In the same manner as in Example [3-1], the concentration of 13S-hydroxy-octadecadienoic acid in the reaction product was measured, and relative values thereof were compared with each other.

As a result, as illustrated in FIG. 8A, it was confirmed that the protein having the amino acid sequence of SEQ ID NO: 1 had better enzyme activity as closer to pH 8.0.

In addition, 10 KU/ml of the protein having the amino acid sequence of SEQ ID NO: 2 purified and isolated in Example [1-2] and 100 μM of linoleic acid reacted with each other at pH 6 to pH 11 and a temperature of 25° C. for 30 minutes, a reaction product was reduced by adding 1 M of sodium borohydride so that the final concentration became 50 mM, and then the reaction was completed by adding 5 μl/ml of acetic acid. At this time, 50 mM of a sodium phosphate buffer in the case of pH 7.0, 50 mM of a Tris-HCl buffer in the case of pH 8.0, and 50 mM of a sodium borate buffer in the case of pH 9.0 to pH 11.0 were used, respectively.

In the same manner as in Example [3-1], the concentration of 13S-hydroxy-octadecadienoic acid in the reaction product was measured, and relative values thereof were compared with each other.

As a result, as illustrated in FIG. 8B, it was confirmed that the protein having the amino acid sequence of SEQ ID NO: 2 had better enzyme activity as closer to pH 8.0.

[4-2] Effect of Temperature

In order to confirm an effect of the temperature, 50 KU/ml of the protein having the amino acid sequence of SEQ ID NO: 1 purified and isolated in Example [1-2] and 100 μM of linoleic acid reacted with each other at pH 7 and a temperature of 20° C. to 50° C. for 30 minutes, a reaction product was reduced by adding 1 M of sodium borohydride so that the final concentration became 50 mM, and then the reaction was completed by adding 5 μl/ml of acetic acid.

In the same manner as in Example [3-1], the concentration of 13S-hydroxy-octadecadienoic acid in the reaction product was measured, and relative values thereof were compared with each other.

As a result, as illustrated in FIG. 9A, it was confirmed that the protein having the amino acid sequence of SEQ ID NO: 1 had better enzyme activity as closer to 20° C.

In addition, 10 KU/ml of the protein having the amino acid sequence of SEQ ID NO: 2 purified and isolated in Example [1-2] and 100 μM of linoleic acid reacted with each other at pH 7 and a temperature of 20° C. to 50° C. for 30 minutes, a reaction product was reduced by adding 1 M of sodium borohydride so that the final concentration became 50 mM, and then the reaction was completed by adding 5 μl/ml of acetic acid.

In the same manner as in Example [3-1], the concentration of 13S-hydroxy-octadecadienoic acid in the reaction product was measured, and relative values thereof were compared with each other.

Figure 9B:
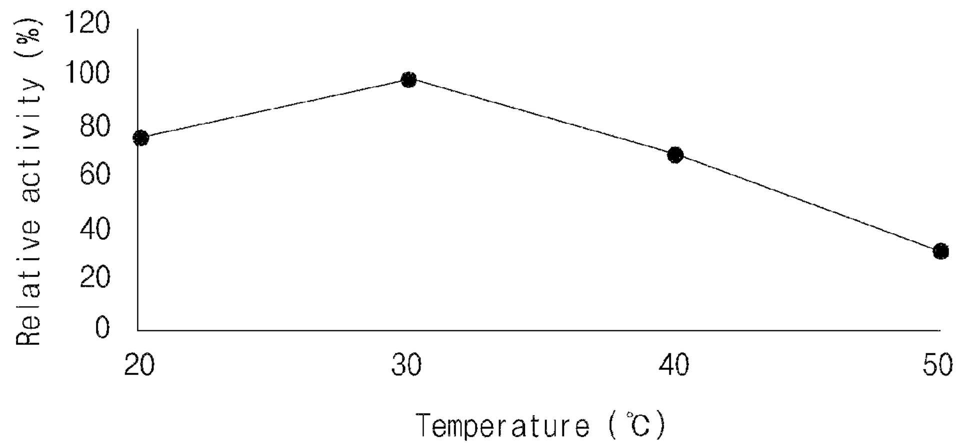
FIG. 9B is a graph showing a result of confirming an effect of a temperature on the enzyme activity of a protein having an amino acid sequence of SEQ ID NO: 2.

As a result, as illustrated in FIG. 9B, it was confirmed that the protein having the amino acid sequence of SEQ ID NO: 2 had better enzyme activity as closer to 30° C.

[4-3] Reaction Rate Under Optimal Conditions

Under optimal conditions confirmed in [4-1] and [4-2] above, $K_m$ and $K_{cat}$ values of the protein having the amino acid sequence of SEQ ID NO: 1 and the protein having the amino acid sequence of SEQ ID NO: 2 were examined. That is, the reaction of the protein having the amino acid of SEQ ID NO: 1 was performed in an environment of pH 8.0 and 20° C., and the reaction of the protein having the amino acid sequence of SEQ ID NO: 2 was performed in an environment of pH 7.0 and 30° C., and the results thereof were shown in Table 4.

TABLE 4

| Protein | $K_m$ (μM) | $K_{cat}$ ($min^{-1}$) |
|---|---|---|
| Protein having amino acid sequence of SEQ ID NO: 1 | 46.82 ± 1.0 | 23.52 ± 1.0 |
| Protein having amino acid sequence of SEQ ID NO: 2 | 79.43 ± 0.8 | 0.4 ± 0.02 |

[Example 5] Confirmation of Effect of Inhibiting Proliferation of Cancer Stem Cells of Multi-Hydroxy Derivatives of Polyunsaturated Fatty Acids Produced by Enzyme Activity of Protein of the Present Invention In Example [3-2] above, the di-hydroxy derivative obtained by hydroxylating docosahexaenoic acid to the protein having the amino acid sequence of SEQ ID NO: 1 of the present invention and the tri-hydroxy derivative obtained by hydroxylating docosahexaenoic acid to the protein having the amino acid sequence of SEQ ID NO: 2 of the present invention were isolated and purified, respectively. The purified derivatives were treated to human beast cancer cells and human beast cancer-derived cancer stem cells and then the effects thereof were confirmed.

More specifically, first, human breast cancer cells MDA-MB-231 (ATCC) were incubated at a density of $1\times10^6$ cells in a 10 cm culture dish with a DMEM medium added with 10% fetal bovine serum (FBS, Hyclone), 100 U/ml penicillin, and 100 μg/ml of streptomycin (carbon dioxide 5%, 37° C.)

The human breast cancer cells MDA-MB-231 were incubated at a density of 0.5 to $1\times10^4$ cells in a ultra-low attachment 6-well plate containing 2 ml of a Complete MammoCult™ medium (StemCell Technologies, Canada) added with 4 μg/ml of heparin, 0.48 μg/ml of hydrocortisone, 100 U/ml of penicillin, and 100 μg/ml of streptomycin (carbon dioxide 5%, 37° C.) to form mammospheres of the human beast cancer-derived cancer stem cells.

To the human breast cancer cells MDA-MB-231 and the mammospheres of the human beast cancer-derived cancer stem cells obtained as described above, the di-hydroxy derivative obtained by hydroxylating docosahexaenoic acid to the protein having the amino acid sequence of SEQ ID NO: 1 of the present invention and the tri-hydroxy derivative obtained by hydroxylating docosahexaenoic acid to the protein having the amino acid sequence of SEQ ID NO: 2 of the present invention in Example [3-2] were treated at the concentration of 0 to 60 μM, respectively.

Figure 10B:
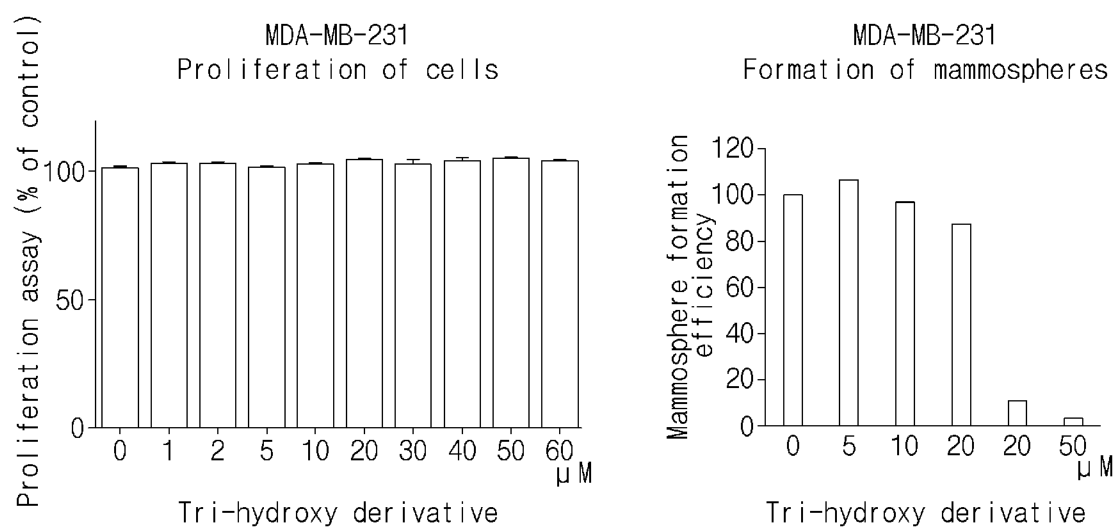
FIG. 10B illustrates a result of analyzing an effect of a tri-hydroxy derivative produced by the protein having the amino acid sequence of SEQ ID NO: 2 on the proliferation of cancer cells and cancer stem cells.

As a result, as shown in FIG. 10A, it was confirmed that by the di-hydroxy derivative obtained by hydroxylating docosahexaenoic acid to the protein having the amino acid sequence of SEQ ID NO: 1 of the present invention, the proliferation of the mammospheres of the beast cancer-derived cancer stem cells was inhibited, whereas in spite of the di-hydroxy derivative at the same concentration, there was no effect on the proliferation of the breast cancer cells. In addition, as shown in FIG. 10B, it was confirmed that by the tri-hydroxy derivative obtained by hydroxylating docosahexaenoic acid to the protein having the amino acid sequence of SEQ ID NO: 2 of the present invention at the concentration of 40 μM or more, the proliferation of the mammospheres of the beast cancer-derived cancer stem cells was inhibited, whereas in spite of the tri-hydroxy derivative at the same concentration, there was no effect on the proliferation of the breast cancer cells.

As described above, while preferred embodiments of the present invention have been illustratively described, the scope of the present invention is not limited only to the specific embodiments described above, and the present invention will be able to be appropriately modified by those skilled in the art within appended claims of the present invention.

The invention claimed is:

1. A compound having a chemical structure of Chemical Formula 2:

[Chemical Formula 2]

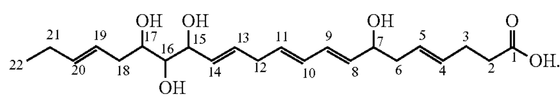

2. A method for inhibiting the proliferation of cancer stem cells in a subject in need thereof, comprising:

combining the compound of claim 1 with a pharmaceutically acceptable substituent to obtain a composition; and administering the composition to the subject.

3. The method of claim 2, wherein the cancer stem cells are obtained from human breast cancer.

4. A method for producing the compound of claim 1, comprising reacting the enzyme having the amino acid sequence of SEQ ID NO: 2 with docosahexaenoic acid (DHA).

* * * * *